United States Patent
Canal et al.

(10) Patent No.: US 9,795,714 B2
(45) Date of Patent: Oct. 24, 2017

(54) FGF-18 FORMULATION IN ALGINATE/COLLAGEN HYDROGELS

(71) Applicant: ARES TRADING S.A., Aubonne (CH)

(72) Inventors: Fabiana Canal, Sacile (IT); Caterina Lo Presti, Rome (IT)

(73) Assignee: ARES TRADING S.A., Aubonne (CH)

( * ) Notice: Subject to any disclaimer, the term of this patent is extended or adjusted under 35 U.S.C. 154(b) by 0 days.

(21) Appl. No.: 15/105,710

(22) PCT Filed: Dec. 23, 2014

(86) PCT No.: PCT/EP2014/079205
§ 371 (c)(1),
(2) Date: Jun. 17, 2016

(87) PCT Pub. No.: WO2015/097236
PCT Pub. Date: Jul. 2, 2015

(65) Prior Publication Data
US 2016/0303291 A1    Oct. 20, 2016

(30) Foreign Application Priority Data
Dec. 24, 2013 (EP) ..................... 13199591

(51) Int. Cl.
| | |
|---|---|
| A61L 27/52 | (2006.01) |
| A61L 27/26 | (2006.01) |
| A61L 27/24 | (2006.01) |
| A61L 27/50 | (2006.01) |
| A61L 27/54 | (2006.01) |
| A61L 27/20 | (2006.01) |
| C07K 14/50 | (2006.01) |
| C07K 14/78 | (2006.01) |
| A61K 31/734 | (2006.01) |
| A61K 38/39 | (2006.01) |

(52) U.S. Cl.
CPC .............. *A61L 27/52* (2013.01); *A61L 27/20* (2013.01); *A61L 27/24* (2013.01); *A61L 27/26* (2013.01); *A61L 27/505* (2013.01); *A61L 27/54* (2013.01); *A61L 2300/414* (2013.01); *A61L 2400/06* (2013.01); *A61L 2430/06* (2013.01)

(58) Field of Classification Search
None
See application file for complete search history.

(56) References Cited

U.S. PATENT DOCUMENTS

2008/0193425 A1* 8/2008 Ellsworth ............ A61K 9/0019
424/93.7
2016/0317668 A1    11/2016 Lo Presti et al.

FOREIGN PATENT DOCUMENTS

| CA | 2 254 350 | 5/2000 |
|---|---|---|
| WO | WO 2004/032849 | 4/2004 |
| WO | WO 2006/044342 | 4/2006 |
| WO | WO 2012/113812 | 8/2012 |
| WO | WO 2012/172072 | 12/2012 |
| WO | WO 2015/097233 | 7/2015 |

OTHER PUBLICATIONS

Written Opinion in International Application No. PCT/EP2014/079205, dated Jul. 24, 2015, pp. 1-6.
Rayatpisheh, S. et al. "Aligned 3D human aortic smooth muscle tissue via layer by layer technique inside microchannels with novel combination of collagen and oxidized alginate hydrogel" Journal of Biomedical Materials Research A, Aug. 2011, pp. 235-244, vol. 98A, No. 2.

* cited by examiner

*Primary Examiner* — David Romero
(74) *Attorney, Agent, or Firm* — Saliwanchik, Lloyd & Eisenschenk

(57) ABSTRACT

The invention relates to the field of pharmaceutical formulations. More particularly, it is directed to homogeneous hydrogels comprising Fibroblast Growth Factor 18 (FGF-18) compound and to methods of producing such hydrogels. The hydrogels of the invention can be used, once formed in situ, for the treatment of cartilage disorders such as osteoarthritis or cartilage injury.

15 Claims, 15 Drawing Sheets

SEQ ID NO:1 (human FGF-18)

MYSAPSACTCLCLHFLLLCFQVQVLVAEENVDFRIHVENQTRARDDVSRKQLRLYQLYSRTSGKHIQVLGRRISA
RGEDGDKYAQLLVETDTFGSQVRIKGKETEFYLCMNRKGKLVGKPDGTSKECVFIEKVLENNYTALMSAKYSGWY
VGFTKKGRPRKGPKTRENQQDVHFMKRYPKGQPELQKPFKYTTVTKRSRRIRPTHPA

Figure 11 a

SEQ ID NO:2 (sprifermin)

MEENVDFRIHVENQTRARDDVSRKQLRLYQLYSRTSGKHIQVLGRRISARGEDGDKYAQLLVETDTFGSQVRIKG
KETEFYLCMNRKGKLVGKPDGTSKECVFIEKVLENNYTALMSAKYSGWYVGFTKKGRPRKGPKTRENQQDVHFMK
RYPKGQPELQKPFKYTTVTK

Figure 11 b

FGF-18 FORMULATION IN ALGINATE/COLLAGEN HYDROGELS

CROSS-REFERENCE TO RELATED APPLICATION

This application is the U.S. national stage application of International Patent Application No. PCT/EP2014/079205, filed Dec. 23, 2014.

The Sequence Listing for this application is labeled "Seq-List.txt" which was created on Jun. 16, 2016 and is 4 KB. The entire content of the sequence listing is incorporated herein by reference in its entirety.

FIELD OF INVENTION

The invention relates to the field of pharmaceutical formulations. More particularly it is directed to Fibroblast Growth Factor 18 (FGF-18) protein formulations in alginate/collagen hydrogels, and to methods of producing such hydrogels/formulations.

BACKGROUND OF THE INVENTION

Fibroblast Growth Factor 18 (FGF-18) is a member of the Fibroblast Growth Factor (FGF) family of proteins, closely related to FGF-8 and FGF-17. Members of the FGF family are characterized by heparin-binding domains. Such a putative heparin-binding domain has been identified for FGF-18. It is postulated that receptor-mediated signaling is initiated upon binding of FGF ligands complexed with cell-surface heparin sulphate proteoglycans.

It has been shown that FGF-18 is a proliferative agent for chondrocytes and osteoblasts (Ellsworth et al., 2002; Shimoaka et al., 2002). FGF-18 has been proposed for the treatment of cartilage disorders such as osteoarthritis (OA) and cartilage injury (CI), either alone (WO2008/023063) or in combination with hyaluronic acid (WO2004/032849).

Pharmaceutical compositions comprising an FGF polypeptide are known from the art. WO2012172072 describes a freeze-dried formulation containing FGF-18, wherein said composition comprises FGF-18, a buffer, a poloxamer surfactant and a sugar as stabilizing agent. Said FGF-18 freeze-dried formulation is showing promising results in the treatment of OA or CI. The current dosing regimen, using said freeze-dried formulation, is a treatment cycle of once weekly injection for 3 weeks. The treatment cycle can be repeated.

In the case of CI, the main drawback of the current formulation is that, once injected intraarticularly (i.a.), the presence of FGF-18 in the synovial fluid may also induce uncontrolled cartilage growth in healthy areas. This can, of course, induce unwanted effects such as reduced joint mobility. The delivery of FGF-18 selectively at the level of the target site could promote the cartilage growth only in the damaged area. In particular, the delivery of FGF-18 at the level of the damaged area could be highly beneficial for the treatment of CI coupled with microfracture. Microfracture is an articular cartilage repair surgical technique that works by creating small fractures in the underlying bone. This causes the release of pluripotent mesenchymal stem cells from the bone marrow (Ringe, J. et al., 2012). Filling the cartilage hole with an injectable gel containing FGF-18 would direct cells within the gel that would then act as mechanical supports for cell growth and drug reservoirs at the same time. For this reason, it would be preferable if FGF-18 is not released from the gel but stays entrapped in the matrix.

A typical approach in tissue engineering is the confinement of growth factors in a 3D matrix, i.e., a scaffold, that can be either implanted or injected, depending on the mechanical properties, in order to assume the shape of the acceptor site. Mandatory characteristics of the scaffold are biocompatibility and resorbability. Additionally, scaffolds must be able to provide cells the ideal environment to grow, proliferate and reform the damaged tissue. Ideally, the matrix should resemble the same mechanical properties as the original tissue and should present a microporosity able to host cells (interconnected pores with a sufficient size) (Tessmar and Göpferich, 2007).

For instance, WO2012113812 describes a nanofibrous scaffold coated with at least one layer of polyanions and one layer of polycations. Therapeutic molecules such as FGF-18 can be included in the scaffold. In particular, the therapeutic molecule can form the polyanion layer. Said scaffold may optionally further comprising osteoblasts within a collagen hydrogel and chondrocytes within an alginate hydrogel, each hydrogel being deposited on the coated scaffold. Said scaffold is to be implanted in situ, via surgery.

Hydrogels are three-dimensional networks of hydrophilic polymer chains able to absorb and retain large amounts of water. Their main feature is that they are able to swell or shrink but not dissolve in aqueous media. Therefore, it is possible to entrap in their matrix an active molecule (an Active Pharmaceutical Ingredient, i.e., API) that is then slowly released or retained, depending on the presence of specific interactions between the matrix and the API (Lo Presti et al., 2011). The advantage of the use of injectable hydrogels for treating a cartilage disorder is the possibility to inject the scaffold by arthroscopy in the cartilage defect, without the need of any invasive surgery making use of solid scaffolds.

Among the diverse hydrogels that are already known, some formulations are based on polymers able to undergo the gelling process in response to a particular physical or chemical stimulus. These are present as viscous injectable liquids that, once injected, turn to macroscopic gels in response to environmental stimuli at the site of injection, such as changes in temperature, pH or ionic strength. The composition of the formulation can be tuned in order to obtain hydrogels with different characteristics, such as viscoelastic properties, microporosity, etc. (WO2008063418; Lo Presti et al., 2011; C. Dispenza et al., 2011). When preparing a pharmaceutical composition comprising a bioactive protein, said composition must be formulated in such a way that the activity of the protein is maintained for an appropriate period of time. A loss in activity/stability of the protein may result from chemical or physical instabilities of the protein, notably due to denaturation, aggregation or oxidation. The resulting products may thus be pharmaceutically unacceptable. Although the use of excipient(s) and/or hydrogel(s) is known to increase the stability of a given protein, the stabilizing effects of these excipients is highly dependent on the polymer in the gels, the nature of the excipients and the bioactive protein itself.

There remains a need for further formulations containing FGF-18 as an active ingredient, wherein said formulations, while keeping the bioactivity of the active ingredient and being suitable for use in injection, preferably for intraarticular injection, allow reduction of the number of injections needed for the treatment. Such a characteristic would allow the reduction of the risk of infections and would increase the patient's convenience as it does not require surgery or invasive implantation. Said formulations could be useful for administration to a patient for the treatment of a cartilage disorder, such as osteoarthritis or cartilage injury.

SUMMARY OF THE INVENTION

It is an object of the present invention to provide a novel formulation containing an FGF-18 protein. More particularly, said formulation is a homogeneous hydrogel containing FGF-18, wherein said hydrogel is preferably an ion-responsive hydrogel, and more preferably an alginate/collagen gel. The invention also provides methods for preparing the homogeneous hydrogel according to the present invention. The hydrogel containing FGF-18, herein described, may be useful for administration in the treatment of cartilage disorders. Of particular interest is an alginate/collagen hydrogel, further containing FGF-18 protein.

In a first aspect, the invention provides a hydrogel (i.e. a gel formulation), which is homogeneous, comprising or consisting of alginate, collagen, FGF-18, and a sugar as an isotonicity/stabilizing agent, as well as a salt. This formulation is provided as 2 component-gelation systems, each system being in a liquid form when separated. Alternatively, the component-gelation system comprising alginate may be in a freeze-dried form. One of the components comprises or consists of a liquid or freeze-dried composition of alginate, collagen, FGF-18, and the sugar (solution 1). The components form a homogeneous composition. The second component comprises or consists of the salt in a liquid form as well (solution 2). Once the 2 component-gelation systems (solution 1 and solution 2) are mixed (or combined) together, the gel forms. Said gel is also homogeneous. In a preferred embodiment, the stabilizing agent is a sugar or a sugar alcohol, such as sucrose, mannitol, trehalose, or D-sorbitol, and the salt is a dicationic salt, such as magnesium salt, copper salt, zinc salt or calcium salt (e.g. calcium chloride). In a preferred embodiment, in the first component-gelation system (i.e., solution 1), the concentration in alginate is at or about 1 to 5% wt, preferably at or about 2.5 to 4.5, even preferably at or about 3 or 4% wt; the collagen is at a concentration at or about 0.1 to 5 µg/mL, preferably at or about 1 or 2 µg/mL; the concentration of sucrose is at or about 10-100 mg/mL, preferably at or about 30-70 mg/mL, such as at or about 30, 40, 50, 60 or 70 mg/mL, even preferably 70 mg/mL; and the concentration of the salt solution, in the second component-gelation system (i.e., solution 2), is at or about 1 to 20 mg/mL, preferably 10 mg/mL. When mixed together, the volume ratio of solution 1:solution 2 is from 5:1 to 1:2, more preferably 2:1 (in the case of a freeze-dried formulation, the volume of solution 1 is considered before the lyophilization process). Preferably, FGF-18 is selected from the group consisting of: 1) a polypeptide comprising or consisting of the mature form of human FGF-18, corresponding to the sequence comprising or consisting of residue 28 (Glu) to residue 207 (Ala) of SEQ ID NO: 1, 2) a polypeptide comprising or consisting of a truncated form of human FGF-18 comprising or consisting of residue 28 (Glu) to residue 196 (Lys) of SEQ ID NO: 1, and 3) a polypeptide comprising or consisting of SEQ ID NO: 2. More preferably, FGF-18 is sprifermin, as defined hereafter. The first component-gelation system may further comprise a buffer, and/or optionally other excipients.

Solution 1 is preferably to be co-injected with solution 2 to form a hydrogel in situ.

In a second aspect, the invention provides a method for preparing a homogeneous hydrogel of FGF-18, comprising the steps of:

1) preparing solution 1 comprising or consisting of FGF-18, together with alginate, collagen and an isotonicity/stabilizing agent,
2) preparing solution 2 comprising or consisting of a salt, and
3) co-injecting both solutions to form the gel, wherein the isotonicity/stabilizing agent is a sugar or a sugar alcohol, such as sucrose, mannitol, trehalose or D-sorbitol, and the salt is a dicationic salt, such as a magnesium salt, copper salt, zinc salt or calcium salt (e.g., calcium chloride). Preferably the pH of the final formulation is kept at or about 6 to 8, and more particularly at or about 7. In a preferred embodiment, FGF-18 is selected from the group consisting of: 1) a polypeptide comprising or consisting of the mature form of human FGF-18, corresponding to the sequence comprising or consisting of residue 28 (Glu) to residue 207 (Ala) of SEQ ID NO: 1, 2) a polypeptide comprising or consisting of a truncated form of human FGF-18 comprising or consisting of residue 28 (Glu) to residue 196 (Lys) of SEQ ID NO: 1, and 3) a polypeptide comprising or consisting of SEQ ID NO: 2. More preferably, FGF-18 is sprifermin, as defined hereafter. Solution 1 may further comprise a buffer, and/or optionally other excipients.

In a third aspect, the invention provides an article of manufacture for pharmaceutical or veterinary use, comprising:

1) a first container comprising alginate, collagen, FGF-18 protein, and an isotonicity/stabilizing agent (solution 1) (said composition being homogeneous), and
2) a second container comprising a salt (solution 2), wherein the isotonicity/stabilizing agent is a sugar or a sugar alcohol, such as sucrose, mannitol, trehalose or D-sorbitol, and the salt is a dicationic salt, such as a magnesium salt, copper salt, zinc salt or calcium salt (e.g., calcium chloride). Preferably, FGF-18 is selected from the group consisting of: 1) a polypeptide comprising or consisting of the mature form of human FGF-18, corresponding to the sequence comprising or consisting of residue 28 (Glu) to residue 207 (Ala) of SEQ ID NO: 1, 2) a polypeptide comprising or consisting of a truncated form of human FGF-18 comprising or consisting of residue 28 (Glu) to residue 196 (Lys) of SEQ ID NO: 1, and 3) a polypeptide comprising or consisting of SEQ ID NO: 2. More preferably, FGF-18 is sprifermin, as defined hereafter. Solution 1 may further comprise a buffer, and/or optionally other excipients. The content of each container is then mixed together in situ upon simultaneous injection. Preferably, the first container and the second container of the article of manufacture are the two compartments of a dual-chamber or double injection system.

Definitions

The term "FGF-18 protein" or "FGF-18", as used herein, is intended to be a protein maintaining at least one biological activity of the human FGF-18 protein. FGF-18 may be native, in its mature form, or a truncated form thereof. Biological activities of the human FGF-18 protein include, notably, the increase of osteoblastic activity (see WO98/16644) or cartilage formation (see WO2008/023063).

Native, or wild-type, human FGF-18 is a protein expressed by chondrocytes of articular cartilage. Human FGF-18 was first designated zFGF-5 and is fully described in WO98/16644. SEQ ID NO: 1 corresponds to the amino acid sequence of the native human FGF-18, with a signal peptide consisting of amino acid residues 1(Met) to 27(Ala). The mature form of human FGF-18 corresponds to the amino acid sequence from residue 28(Glu) to residue 207 (Ala) of SEQ ID NO: 1 (180 amino acids).

FGF-18, in the present invention, may be produced by a recombinant method, such as taught by WO2006/063362. Depending on the expression systems and conditions, FGF-18 in the present invention is expressed in a recombinant host cell with a starting Methionine (Met residue) or with a signal sequence for secretion. When expressed in a prokaryotic host, such as in *E. coli*, FGF-18 contains an additional Met residue in the N-terminal of its sequence. For instance, the amino acid sequence of human FGF-18, when expressed in *E. coli*, starts with a Met residue in N-term (position 1) followed by residues 28 (Glu) to residue 207 (Ala) of SEQ ID NO: 1.

The term "truncated form" of FGF-18, as used herein, refers to a protein which comprises or consists of residues 28 (Glu) to 196 (Lys) of SEQ ID NO: 1. Preferably, the truncated form of FGF-18 protein is the polypeptide designated "trFGF-18" (170 amino acids), which starts with a Met residue (in the N-terminal) followed by amino acid residues 28 (Glu)-196 (Lys) of the wild-type human FGF-18. The amino acid sequence of trFGF-18 is shown in SEQ ID NO: 2 (amino acid residues 2 to 170 of SEQ ID NO: 2 correspond to amino acid residues 28 to 196 of SEQ ID NO: 1). trFGF-18 is a recombinant truncated form of human FGF-18, produced in *E. coli* (see WO2006/063362). The International Nonproprietary Name (INN) for this particular form of FGF-18 is sprifermin. Sprifermin has been shown to display similar activities to the mature human FGF-18, e.g., it increases chondrocyte proliferation and cartilage deposition, leading to repair and reconstruction of a variety of cartilaginous tissues (see WO2008/023063).

The terms "active molecule" and "active ingredient" relate to an Active Pharmaceutical Ingredient, i.e., API. The preferred API, in the context of the present invention, is FGF-18.

The term "gel" or "hydrogel" is used interchangeably in this application. They refer to a 3D matrix, or scaffold, useful as a pharmaceutical formulation. They are not solid scaffolds.

The term "homogeneous" means that the various components of the formulation are mixed, blended, stirred or melted together, i.e., they do not form separate layers of components.

The term "alginate", also known as alginic acid or algin, refers to any form of alginate. It is a well-known gelating agent, notably when used with a dicationic salt. One of the forms that can be used in the context of the present invention is sodium alginate.

The term "collagen" refers to a group of naturally occurring proteins. Although nearly 30 different forms of collagen exist, the main one is collagen of type I. Collagen of type I as well as collagen of type II are the preferred forms that can be used in the context of the present invention. However, other forms of collagen can be used.

The term "alginate/collagen" as used in the present application refers to a combination of alginate and collagen.

The term "dicationic salt" refers to but is not limited to a salt comprising magnesium, copper, zinc or calcium, for instance. Included are magnesium chloride, copper chloride, zinc chloride or calcium chloride. Preferably, the dicationic salt according to the invention is not a polycationic salt, nor derived from a polycationic component (such as those disclosed in WO2012/113812).

The term "stable" solution or formulation, as used herein, is one solution or formulation wherein the degree of degradation, modification, aggregation, loss of biological activity and the like of proteins therein is acceptably controlled, and does not increase unacceptably with time. Preferably, the formulation retains at least more than 80% of the FGF-18 activity over a period of at least 12 months at room temperature. The stabilized formulation of the present invention comprising FGF-18 preferably has a shelf-life of at least about 12 months, 18 months, or more preferably at least 20 months, still more preferably about 24 months, when stored at room temperature or at 2-8° C., for instance. Methods for monitoring the stability of the FGF-18 formulation of the present invention are available in the art.

The term "stabilizing agent", "stabilizer" or "isotonicity agent", as used herein, is a compound that is physiologically tolerated and imparts a suitable stability/tonicity to a formulation. It notably prevents the net flow of water across cell membranes that are in contact with the formulation. During freeze-drying (lyophilization) process, the stabilizer is also effective as a cryoprotectant (i.e., lyoprotectant). Compounds such as glycerin are commonly used for such purposes. Other suitable stability agents include, but are not limited to, amino acids or proteins (e.g., glycine or albumin), salts (e.g., sodium chloride), and sugars or sugar alcohols (e.g., dextrose, mannitol, trehalose, sucrose, D-sorbitol or lactose). According to the present invention, the preferred stabilizing/tonicity agent is a sugar, even more preferably sucrose.

The term "buffer", as used herein, refers to solutions of compounds that are known to be safe in formulations for pharmaceutical or veterinary use and that have the effect of maintaining or controlling the pH of the formulation in the pH range desired for the formulation. Acceptable buffers for controlling pH at a moderately acidic pH to a moderately basic pH include, but are not limited to, phosphate, acetate, citrate, arginine, TRIS, and histidine buffers. "TRIS" refers to 2-amino-2-hydroxymethyl-1,3,-propanediol, and to any pharmacologically acceptable salt thereof. A preferred buffer can be a histidine buffer.

The term "solvent", as used herein, refers to a liquid solvent, either aqueous or non-aqueous. The selection of the solvent depends notably on the solubility of the drug compound in said solvent and on the mode of administration. Aqueous solvents may consist solely of water, or may consist of water plus one or more miscible solvents, and may contain dissolved solutes such as sugars, buffers, salts or other excipients. The more commonly used non-aqueous solvents are the short-chain organic alcohols, such as methanol, ethanol, propanol, short-chain ketones, such as acetone, and poly alcohols, such as glycerol. According to the present invention, the preferred solvent is an aqueous solvent such as water or a saline solvent.

The term "vial" or "container", as used herein, refers broadly to a reservoir suitable for retaining the alginate/collagen in a liquid form or in a freeze-dried form. Similarly, it will retain the liquid salt mixture. Examples of a vial that can be used in the present invention include syringes, ampoules, cartridges, or other such reservoirs suitable for delivery of the FGF-18 formulation to the patient via injection, preferably via intra-articular injection. Alternatively, the vial retaining the alginate/collagen solution and the one retaining the salt are presented as the 2 compartments of a dual-chamber system (for example, a syringe or cartridge, a dual-chamber syringe or dual-needle injection device, etc.). Vials suitable for packaging products for intra-articular administration are well known and recognized in the art.

The term "cartilage disorder", as used herein, encompasses disorders resulting from damage due to traumatic injury or chondropathy. Examples of cartilage disorders that may be treated by the administration of the FGF-18 formulation described herein include, but are not restricted to, arthritis, such as osteoarthritis or rheumatoid arthritis, and cartilage injury.

The term "osteoarthritis" is used to intend the most common form of arthritis. It may be caused by the breakdown of cartilage. Bits of cartilage may break off and cause pain and swelling in the joints between bones. Over time the cartilage may wear away entirely, and the bones will rub together. Osteoarthritis can affect any joint but usually concerns the hands and weight-bearing joints such as the hips, knees, feet, and spine. In a preferred example, the osteoarthritis may be knee osteoarthritis or hip osteoarthritis. The skilled person is fully aware of osteoarthritis classifications that are used in the art, in particular the OARSI assessment system (see, for instance, Custers et al., 2007). Osteoarthritis is one of the preferred cartilage disorders that can be treated by administering the FGF-18 formulations according to the present invention.

The term "cartilage injury" as used herein is a cartilage disorder or cartilage damage resulting notably from a trauma. Cartilage injuries can occur as a result of traumatic mechanical destruction, notably further to an accident or surgery (such as microfracture techniques). Also considered within this definition is sport-related injury or sport-related wear of tissues of the joint.

The term "µg" or "mcg" is used interchangeably and refer to a division of the SI unit for mass.

DETAILED DESCRIPTION OF THE INVENTION

The main object of the present invention is an alginate/collagen gel formulation (or hydrogel) comprising or consisting of an alginate, a collagen, an FGF-18 protein, a sugar as stabilizing agent, and a salt. Said hydrogel is homogeneous. The hydrogel may further comprise a buffer, and/or optionally other excipients. In a preferred embodiment, the stabilizing agent is a sugar or a sugar alcohol such as sucrose, mannitol, trehalose or D-sorbitol and the salt is a dicationic salt such as a magnesium salt, copper salt, zinc salt or calcium salt (e.g., calcium chloride). Said hydrogel is suitable for injection at the cartilage level. Preferably, the FGF-18 protein is selected from the group consisting of: 1) a polypeptide comprising or consisting of the mature form of human FGF-18, corresponding to the sequence comprising or consisting of residue 28 (Glu) to residue 207 (Ala) of SEQ ID NO: 1, 2) a polypeptide comprising or consisting of a truncated form of human FGF-18 comprising or consisting of residue 28 (Glu) to residue 196 (Lys) of SEQ ID NO: 1, and 3) a polypeptide comprising or consisting of SEQ ID NO: 2. More preferably, FGF-18 is sprifermin.

The advantage of the use of injectable homogeneous hydrogels is the possibility to inject the scaffold (or the component of the scaffold), already containing FGF-18, in the cartilage defect, without the need of any invasive surgery making use of solid scaffolds. Preferably, such injection of the hydrogel is made by arthroscopy Most preferably, the homogeneous hydrogels according to the present invention are prepared from two solutions, one containing the polymer (herein an alginate system, solution 1) and the other containing the ions (herein in the form of a salt, solution 2), and are formed in situ, upon injection, by mixing (or combining) the 2 solutions. The mixing (or combining) of the 2 solutions is preferably done via co-injection. Solution 1 may further comprise a buffer, and/or optionally other excipients.

In a preferred embodiment, the present invention is directed to the use of homogenous liquid polymeric solutions able to undergo a gelation process, once administered, due to ion concentration variations. In an alternative embodiment, the polymeric solution can be in a freeze-dried form. When the polymeric solution is in such a freeze-dried form, said solution may optionally further comprise a lyoprotectant. Known lyoprotectants are, for instance, sugars, and polyols in general, such as sucrose, mannitol, trehalose or D-sorbitol.

Should solution 1 be in a freeze-dried form, the lyophilization is preferably carried out using conventional procedures.

The concentration of FGF-18, in solution 1, is preferably at or about 0.1 to 300 mcg/mL, preferably at or about 0.1, 1, 5, 10, 20, 30, 40, 50, 54, 60, 70, 80, 90, 100, 150, 200, 250 or 300 mcg/mL. More preferably FGF-18 is at a concentration at or about 0.1 to 100 mcg/mL, even more preferably at or about 10 to 60 mcg/mL. FGF-18 can be added in excess of 5%, in order to prevent possible protein losses that could occur during formulation. For instance, for an FGF-18 concentration of 30 mcg/mL, the compound can be added in an amount of 31.5 mcg/mL. The gelation component in solution 1, i.e., alginate, is at a concentration at or about 1 to 5% wt, preferably at or about 2.5 to 4.5% wt, even preferably at or about 3 or 4% wt.

The stabilizing agent in the present invention is preferably a sugar or a sugar alcohol, such as sucrose, mannitol, trehalose or D-sorbitol. The preferred sugar is sucrose. Preferably, the concentration of the stabilizing agent in solution 1 is at or about 10 to 100 mg/mL, more preferably at or about 30-70 mg/mL, such as at or about 30, 40, 50, 60 or 70 mg/mL, even preferably at or about 70 mg/mL.

The collagen according to the present invention, in solution 1, is preferably at a concentration at or about 0.1 to 5 mcg/mL, more preferably at or about 1 to 2 mcg/mL, more particularly at or about 1 or 2 mcg/mL.

The salt, in the second component-gelation system (i.e., solution 2), is preferably a dicationic salt such as a magnesium salt, copper salt, zinc salt or calcium salt (e.g., calcium chloride). The concentration of the salt solution is at or about 1 to 20 mg/mL, preferably at or about 10 mg/mL.

In a preferred embodiment, solution 1 comprising or consisting of FGF-18 at or about 0.1-100 mcg/mL, alginate at or about 4% wt, sucrose at or about 70 mg/mL and collagen at or about 2 mcg/mL, and solution 2 comprising or consisting of a dicationic salt (such as calcium chloride) at or about 10 mg/mL. Solution 1 may further comprise a buffer, and/or optionally other excipients. Solution 1 is homogeneous.

When mixed together, the volume ratio of solution 1:solution 2 is from 5:1 to 1:2, more preferably 2:1 (in case of freeze-dried formulation, the volume of solution 1 is considered before the lyophilization process).

Once mixed together, the final concentrations of each component are preferably as follows:
  FGF-18: from 0.00006 to 0.2% w/v, such as 0.0036% w/v (when FGF-18 is at 0.1-300 mcg/mL before mixing, based on the FGF-18 concentration given in the examples section);
  alginate: from 0.6 to 3.33% w/v, such as 2.67% w/v (when alginate is at 4% w/v before mixing);
  collagen: from 0.00006 to 0.003% w/v, such as 0.000133% w/v (when collagen is at 2 mcg/mL before mixing);

stabilizing agent: from 0.6 to 6% w/v, such as 4.67% w/v (when sucrose, for instance, is at 70 mg/mL before mixing); and dicationic salt: from 0.033 to 0.66% w/v, such as 0.33% w/v (when the salt is at 10 mg/mL before mixing).

In a preferred embodiment, the pH of the final formulation is kept at or about 6 to 8, more particularly at or about 7.

The invention further provides a method for preparing the homogeneous hydrogels of FGF-18, comprising the steps of:
1) preparing a first solution (solution 1) comprising or consisting of FGF-18, together with alginate, collagen and a stabilizing agent,
2) preparing a second solution (solution 2) comprising or consisting of a salt, and
3) co-injecting both solutions to form the gel, wherein the stabilizing agent is a sugar or a sugar alcohol, such as sucrose, mannitol, trehalose or D-sorbitol, and the salt is a dicationic salt, such as a magnesium salt, copper salt, zinc salt or calcium salt (e.g., calcium chloride). Solution 1 may further comprise a buffer, and/or optionally other excipients. Solution 1 is homogeneous. In a preferred embodiment the pH of the final formulation is kept at or about 6 to 8, and more particularly at or about 7. Preferably, FGF-18 is selected from the group consisting of: 1) a polypeptide comprising or consisting of the mature form of human FGF-18, corresponding to the sequence comprising or consisting of residue 28 (Glu) to residue 207 (Ala) of SEQ ID NO: 1, 2) a polypeptide comprising or consisting of a truncated form of human FGF-18 comprising or consisting of residue 28 (Glu) to residue 196 (Lys) of SEQ ID NO: 1, and 3) a polypeptide comprising or consisting of SEQ ID NO: 2. More preferably, FGF-18 is sprifermin, as defined herein.

Each of the compounds (i.e. FGF-18, alginate, collagen, the stabilizing agent and the salt) can be used according to any one of the concentrations, pH, and/or ratios above described. Preferably, the solution 1:solution 2 ratio (volume to volume, i.e., v:v) is at or about 1:2 to 5:1, more preferably at or about 2:1 (in case of freeze-dried formulation, the volume of solution 1 is considered before the lyophilization process).

When the solution 1 of the hydrogel of the invention is in a freeze-dried form, it has to be reconstituted before step 3) (i.e., before co-injection).

In a third aspect, the invention provides an article of manufacture for pharmaceutical or veterinary use, comprising:
1) a first container comprising or consisting of an alginate, a collagen, an FGF-18 protein, and a stabilizing agent (solution 1), and
2) a second container comprising or consisting of a salt (solution 2), wherein the stabilizing agent is a sugar or a sugar alcohol, such as sucrose, mannitol, trehalose or D-sorbitol, and the salt is a dicationic salt such as a magnesium salt, copper salt, zinc salt or calcium salt (e.g., calcium chloride). Solution 1 may further comprise a buffer, and/or optionally other excipients. Solution 1 is homogenous. Preferably, FGF-18 is selected from the group consisting of: 1) a polypeptide comprising or consisting of the mature form of human FGF-18, corresponding to the sequence comprising or consisting of residue 28 (Glu) to residue 207 (Ala) of SEQ ID NO: 1, 2) a polypeptide comprising or consisting of a truncated form of human FGF-18 comprising or consisting of residue 28 (Glu) to residue 196 (Lys) of SEQ ID NO: 1, and 3) a polypeptide comprising or consisting of SEQ ID NO: 2. More preferably, FGF-18 is sprifermin, as defined herein.

Each of the compounds (i.e., FGF-18, alginate, collagen, the stabilizing agent and the salt) can be used according to any one of the concentrations, pH, and/or ratios above described. Preferably, the solution 1: solution 2 volume ratio (v:v) is at or about 1:2 to 5:1, more preferably at or about 2:1 (in case of freeze-dried formulation, the volume of solution 1 is considered before the lyophilization process). The content of each container is then mixed together in situ upon simultaneous injection (e.g., co-injection).

Preferably, the container retaining the FGF-18 formulation and the one retaining the salt correspond to the two compartments of a dual-chamber system or a dual injection system (syringe or cartridge, for example).

When the polymeric solution (i.e., solution 1) is in a freeze-dried form, the article of manufacture can further comprise a third container comprising or consisting of the solvent, such as water or a saline solution (e.g., 0.9% w/v sodium chloride for injection), needed for reconstitution.

Also described is a packaging material providing instructions to form the hydrogel according to the present invention, preferably in situ.

Importantly, it was surprisingly shown by the inventors (see the Examples section) that when the gels were formed using a syringe connector that allowed for the contemporary injection of the two solutions, no remaining liquid phase was observed at any polymer concentration. In fact, the contextual injection of the two solutions allows for a faster and more homogeneous mixing of the two flows, leading to instantaneous gelation.

The different components of the hydrogel of the invention may be stored for at least about 12 months to about 24 months. Under preferred storage conditions, before the first use, the formulations are kept away from bright light (preferably in the dark), at refrigerated temperatures (at or about 2-8° C.).

The hydrogel of the invention needs to be prepared during injection.

When solution 1 of the hydrogel of the invention is in a freeze-dried form, it has to be reconstituted before use. It is preferably reconstituted under sterile conditions, with a solvent, such as water or a saline solution (e.g., 0.9% w/v sodium chloride for injection) prior to use, i.e., prior to combination (or mixing) with solution 2, and thus prior to injection. After reconstitution, the volume is preferably the same as before lyophilization, such as from about 0.5 mL to 5 mL, more preferably at or about 0.5, 1 or 2 mL. The system has to be allowed to dissolve and homogenized, for instance during 30 minutes, before it becomes ready for injection. Said solution should be used preferably within one hour of reconstitution.

The present invention provides homogeneous hydrogels comprising FGF-18, in particular for single use, suitable for pharmaceutical or veterinary use. The hydrogels comprising FGF-18, according to the present invention, can be used for administration for improving cartilage repair or for the treatment of cartilage disorders, such as osteoarthritis or cartilage injuries.

These homogenous hydrogels are suitable for use in injection and alternative delivery systems. In a particularly preferred embodiment, the formulations of the invention are for intra-articular (i.a.) injection. They can be administered by direct injection into the defect, wherein the gel is preferably formed in situ. In a preferred embodiment of the present invention, the i.a. administration is done in a joint selected from joint of the hip, knee, elbow, wrist, ankle, spine, feet, finger, toe, hand, shoulder, rib, shoulder blade, thigh, shin, heel and along the bony points of the spine. In yet another preferred embodiment the i.a. administration is done in the joint of the hip or the knee.

The following examples are provided to further illustrate the preparation of the formulations and hydrogels of the invention. The scope of the invention shall not be construed as merely consisting of the following examples.

DESCRIPTION OF THE FIGURES

FIGS. 11a and 11b: Sequence of human FGF-18, corresponding to SEQ ID NO: 1 (a) and sequence of sprifermin corresponding to SEQ ID NO: 2 (b).

FIG. 16 b: influence of shear rate on intrinsic shear viscosity of the freeze-dried formulation (FD) at time 0 and after 3-month stability in normal storage conditions (5° C.), accelerated conditions (25° C.) and stressed conditions (40° C.).

FIG. 17 a: Storage modulus (G') variation of the freeze-dried (FD) formulation over time in 3-month stability in normal storage conditions (5° C.), accelerated conditions (25° C.) and stressed conditions (40° C.). FIG. 17 b: Frequency sweep test performed on freeze-dried formulation (FD) at time zero and after 3-month stability in normal storage conditions (5° C.), accelerated conditions (25° C.) and stressed conditions (40° C.).

DESCRIPTION OF THE SEQUENCES

Figure 1:
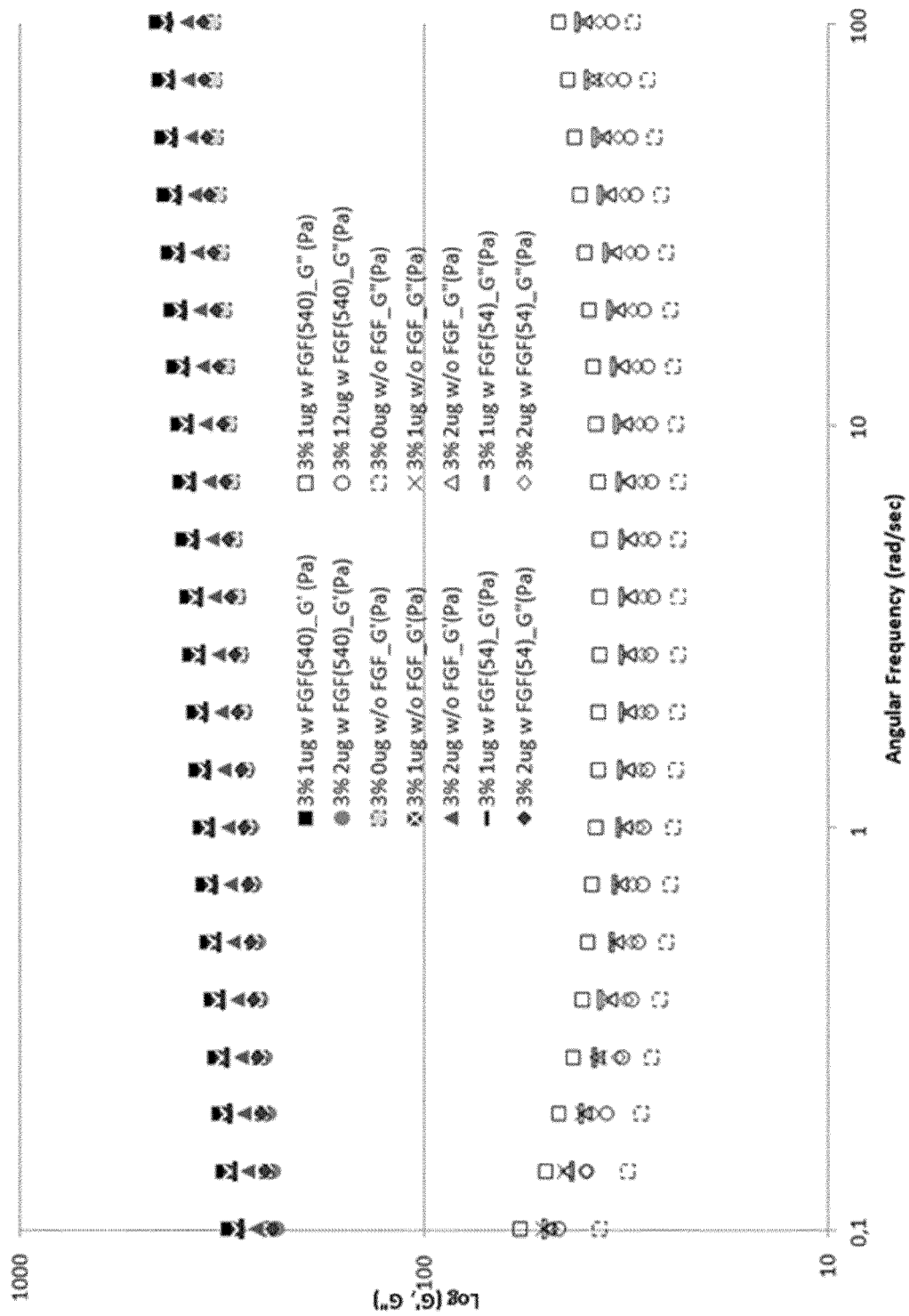
FIG. 1: Frequency sweep test performed on 3% wt alginate-based gel placebo (w/o FGF), with FGF-18 54 mcg/mL in the alginate solution (w FGF (54)) and with FGF-18 540 mcg/mL in the alginate solution (w FGF (540)).

SEQ ID NO: 1: Amino acid sequence of the native human FGF-18.

SEQ ID NO: 2: Amino acid sequence of the recombinant truncated FGF-18 (sprifermin).

EXAMPLES

Materials

The recombinant truncated FGF-18 (trFGF-18 or sprifermin) of the present examples has been prepared in house by expression in *E. coli*, according to the technique described in WO2006/063362. In the following examples, sprifermin and FGF-18 are used interchangeably.

Other main substances used in the examples are the following:

Sodium alginate, Sigma-Aldrich A2158,
Sodium alginate, FMC BioPolymer Keltone LVCR (PharmaGrade Alginate),
Sucrose, Merck 1.07653.9029,
Collagen type I from human skin, Calbiochem 234149, and Calbiochem 234138,
Calcium chloride (CaCl2), Merck 1.02382.0250,
D-(+)-gluconic acid δ-lactone, Sigma-Aldrich G4750,
Chitosan 75% DD HMW, Sigma-Aldrich 419419,
Chitosan 95% DD LMW, Faravelli 43000, and
Chitosan 95% DD HMW, Heppe medical 24711.

The following examples report the preparation and characterization of two kinds of hydrogels, i.e., ion-responsive and temperature-responsive hydrogels. Ion-responsive hydrogels have notably been prepared with sodium alginate, able to form hydrogels in the presence of divalent cations, while temperature-sensitive hydrogels have notably been prepared with chitosan, well-known to be a temperature-sensitive polysaccharide (Tomme et at, 2008). Both polymers used in this study are biocompatible natural polysaccharides.

In order to distinguish clearly in this section between the formulation before the gelation process and the formulation after a gel is formed, the former has been referred to as "liquid solution" and the latter as "gel".

Methods

Gelation Time and Temperature

The gelation time was evaluated for all the formulations by "tilting test". Gels were prepared in glass Petri dishes with 3 cm diameter and incubated at different temperatures. At predetermined time intervals, the Petri dishes were tilted and the gelation time was considered as the time at which the formulation did not show any flowing.

Mechanical Properties

Rheological properties of hydrogels were investigated using an AR 2000 rheometer (TA Instruments) with a cone-plate geometry (1° slope) with 40 mm diameter. Abrasive disks were applied on both plates in order to avoid samples sliding during the test. The thickness of all samples was comprised between approximately 1-2 mm, depending on the sample volume. A solvent trap was used to maintain a water-saturated atmosphere to prevent the evaporation of solvent during the measurement.

After complete swelling of hydrogels from their original liquid solutions in Petri dishes, samples were placed on the rheometer and equilibrated at 37° C. for 2 minutes. Then samples were tested under frequency sweep tests over a range of frequencies from 0.1 to 100 rad/s. The oscillatory stress was set at 10 Pa and the storage, G', and loss, G", moduli were recorded as a function of frequency.

Swelling Behavior Assay

One of the typical properties of the hydrogels is their ability to swell in the presence of an aqueous solution due to their hydrophilic nature. To evaluate the swelling behavior of the gels, they were dipped into a mock synovial fluid (MSF) solution and weighed over time. The experiments were conducted in triplicate in 12-well plates equipped with hanging inserts having a 0.4 μm porous membrane at the bottom.

Only alginate gels were selected for this test. The gels were prepared in 5 mL vials by mixing 200 μL of calcium chloride solution and 400 μL of polymer liquid solution, prepared as described in Example 2, and incubated at 37° C. for 30 minutes. The gels were then transferred into previously weighed empty inserts. Inserts with gel samples were weighed and the corresponding weight was considered as the time 0 reference weight. The inserts containing the gels were placed into the plate and 1.5 mL of the MSF was added into the well, making sure that the porous bottom of the insert was dipped in the solution. The plate was well closed with Parafilm to avoid evaporation phenomena and incubated at 37° C. in the orbital shaker. At predetermined time points, the inserts containing the gels were removed from the wells. The excess MSF was removed by blotting the porous bottom with filter paper and the inserts with gels were then weighed. The solutions in the wells were collected, stored at −80° C. and replaced with fresh MSF. The composition of the MSF was: PBS buffer 1×, pH 7.3, F68 (i.e., poloxamer 188) 0.25 g/L, human serum albumin (HSA) 1% wt, Pen-Strep 1% wt. Prior to use, the MSF was filtered through 0.22 μm filters. Results were reported as swelling ratio, i.e., the ratio between the weight at time t and the weight at time t=0.

Scanning Electron Microscopy (SEM) Analysis

Scanning electron microscopy technique was used to analyze the three-dimensional structure of the polymeric network once the gel is formed. Active alginate-based gels were prepared in a glass Petri dish with 3 cm diameter following the procedure reported in the paragraph related to "gelation time", mixing 1 mL of polymer liquid solution and 0.5 mL of calcium solution. The obtained gel was then incubated at 37° C. for 30 minutes. Six samples were prepared starting from polymer liquid solution at concentrations of 3% wt or 4% wt of alginate, both containing either 0, 1 or 2 μg/mL of collagen type I. Gels were then lyophilized during 48 hours. The freeze-drying cycle comprised a freezing step, a primary drying step and a secondary drying step. During the freezing step, a temperature ramp from room temperature to −45° C. was applied, followed by a stage at −45° C. during 4 hours. This was followed by a primary drying step, when a temperature ramp from −45° C. to −10° C. with a rate of 1° C./min at 50 mTorr pressure was applied, followed by a stage at −10° C. and 50 mTorr during 24 hours and 30 minutes. The secondary drying step comprised two stages: a first temperature ramp from −10° C. to 21° C. with a rate of 1° C./min at 50 mTorr pressure was applied, followed by a stage at 21° C. and 50 mTorr during 12 hours and 30 minutes, and then a second temperature ramp from 21° C. to 37° C. with a rate of 1° C./min at 50 mTorr was applied, followed by a stage at 37° C. and 50 mTorr during 6 hours. Finally, room temperature and atmospheric pressure were reached. Each sample was then stained and analyzed by SEM.

In Vitro Release Study

The same samples used for swelling tests were also analyzed for the in vitro release tests. In particular, the collected phases stored at −80° C. (as described in the above section "Swelling behavior assay") were analyzed by HPLC. Selected samples were also analyzed by Biacore (data not shown).

Ex Vivo Test in an Animal Model

Preliminary tests in an ex vivo animal model were performed to investigate the ability of the alginate formulation to adhere to a real knee joint. The tested formulation was chosen on the basis of the results of the cell invasion assay, reported in Example 9. In particular, the model used consisted of the upper part of the shinbone and the lower part of the thighbone constituting a cow knee. Holes of 1 cm depth and of 0.4 cm diameter were made on both parts of the knee using a corer, in order to mimic the holes made by surgeons when performing microfracture. The holes were then filled with the 4% wt alginate formulation containing final concentrations of 1.3 μg/mL collagen type I and 36 μg/mL FGF-18 in the gel. The test was performed using a valve for infusion in order to connect two different syringes, one containing the alginate solution and one containing the calcium solution. The plungers of the two syringes were pushed at the same time so that the valve was able to mix the solutions. The formulation was injected in the holes both in upright and upside-down positions, to verify the possibility of administration in the different possible real scenarios in vivo. After approximately 2 hours of incubation at 37° C., the gel was removed from the hole to verify its status by visual inspection.

In Vitro Bioassay

A 96-well plate for luminometry (assay plate) is coated with 50 μL/well of sodium alginate 4% solution and 25 μL/well of $CaCl_2$ 10 mg/mL solution, and incubated for 30 minutes at 37° C., 5% $CO_2$ to allow the formation of basal hydrogel.

A 96-well plate (master plate) is dispensed with 160 μL/well of assay medium from row B to row H. Then FGF-18 reference standard and samples are diluted at 10 μg/mL in assay medium and added in triplicate (100 μL/well) in row A, considering the groups of columns as replicates. By using a multi-channel pipette, 1:5 serial dilutions are performed from the well in row A to the well in row H, transferring 40 μL from row A to row H.

From the master plate 25 μL/well of FGF-18 reference standard dilutions are transferred to a basal hydrogel-coated 96-well plate (assay plate) and incubated for 1 hr at 37° C. and 5% $CO_2$.

BaF3/FGFR3c cell cultures, seeded at 10,000,000 SM in a 75 $cm^2$ flask and starved for 24 hrs before the assay, are diluted at 800,000 cells/mL in assay medium and then 25 μL/well are added (20,000 cells/well) in each well to the FGF-18 and basal hydrogel-coated plate for 48 hrs at 37° C. and 5% $CO_2$.

100 μL/well of the "ATPlite 1 step" reagent are added to reveal the proliferation, slowly mixing the plate and reading the emitted luminescence with a luminescence counter.

Example 1: Pre-Formulations

During the pre-formulation work, either alginate or chitosan were mixed with other excipients in order to obtain aqueous solutions with an acceptable osmolality for i.a. injections (target: 350 mOsm/Kg). The liquid solutions were then tested for their gelation time and temperature. Formulations able to form hydrogels within 5 minutes and/or at a temperature around 37° C. were further formulated with FGF-18 at different concentrations (data not shown).

Example 2: Preparation of Ion-Responsive Gels (Alginate)

Generalities

Sodium alginate was used to obtain an ion-responsive gel, as in the presence of divalent cations working as cross-linking agent between the polymer chains, such as $Ca^{2+}$, it is able to form a polymeric network giving rise to a hydrogel. The formulation consisted of two solutions, one containing the polymer and the other containing the ions. Once mixed together, the solutions formed a gel.

The calcium solution was the same for both placebo and active gels and consisted of a solution of calcium chloride $CaCl_2$ in Milli-Q water at a concentration of 10 mg/mL. In the polymer liquid solution, in addition to alginate, collagen type I and the active molecule were added (here, sprifermin), as well as sucrose for adjusting the osmolality value. Placebo polymer liquid solution was prepared as follows: a solution of sucrose in Milli-Q water at a concentration of 70 mg/mL was prepared and used to dissolve sodium alginate at a concentration of either 3% wt or 4% wt, under stirring. Once alginate was solubilized, a solution of collagen type I, dissolved in hydrochloric acid and diluted in Milli-Q water to a concentration of 30 μg/mL or 60 μg/mL, was added under stirring, in order to obtain a collagen concentration in the polymer liquid solution of 1 μg/mL or 2 μg/mL, respectively. For the preparation of active polymer liquid solution, alginate at a concentration of 3% wt or 4% wt was dissolved with a solution of sucrose in Milli-Q water at concentration of 70 mg/mL containing bulk FGF-18 at a concentration of 54 μg/mL. Then the same procedure reported for the placebo was followed for the addition of collagen type I. Gels were prepared by mixing the polymer liquid solution with the calcium solution in the ratio 2:1 (v:v). Prior to further characterization, gels were incubated at 37° C. for 30 minutes.

Preliminary Screening of Placebo Formulations

After testing that the physiological ion amount was not enough to promote the gelation process, divalent cation $Ca^{2+}$ was chosen as a cross-linking agent, in the form of calcium chloride. To avoid the use of calcium, possibly responsible for unwanted calcification phenomena, magnesium chloride was also tested, but the attempt was less successful.

A screening of the possible formulations was then carried out and a preliminary placebo formulation was selected. Different parameters were considered and changed during the screening, such as alginate concentration, $CaCl_2$ concentration, ratio between the volumes of polymer and calcium solutions, and presence of other excipients, such as D-(+)-gluconic acid δ-lactone, used as retardant for gelation, or HSA, added to PBS to better mimic the physiological conditions. It was found that the presence of HSA or D-gluconic acid had no significant effect on the resulting gel and they were therefore discarded, to avoid addition of non-useful components.

It was also observed that the optimal alginate concentration among the tested values was from 2.5 wt % to 4.5 wt %, and notably 3% wt or 4% wt. Indeed, lower alginate concentrations, namely 1% wt or 2% wt, were not applicable, as no complete gel formation was registered. On the other hand, too high alginate concentration (5% wt) led to a very viscous polymer liquid solution, very difficult to handle.

The selected preliminary placebo formulation consisted of a liquid solution of alginate at a concentration of 3% wt in water and a calcium solution of $CaCl_2$ at a concentration of 10 mg/mL in PBS in the ratio 2:1 (v:v).

Addition of FGF-18

To obtain the active formulation, tests on the addition of FGF-18 to the two solutions were carried out. In all the following tests, the ratio between the two solutions was kept constant at 2:1 vol/vol alginate solution to calcium solution. The addition of FGF-18 to the alginate solution caused precipitation phenomena, detected by visual inspection. As a possible solution, alginate was dissolved in PBS buffer containing 0.25 g/L of F68 surfactant. Precipitation, though, was still occurring. To overcome this issue, FGF-18 was added to the buffer before the solubilization of alginate. This way, the precipitation in the polymer solution was avoided and the protein was homogenously distributed, but the physical consistency of the resulting gel looked compromised, compared to the placebo prepared in water. In addition, microscopic precipitation was found anyway, analyzing the residual liquid phase after gel formation. Further investigations proved that precipitation was caused by interaction between $CaCl_2$ and PBS, likely leading to the formation of calcium phosphate. For this reason, PBS was eliminated from both the polymer liquid solution and calcium solution, and only Milli-Q water was used as a solvent.

Optimization of the Formulation

An increase in the alginate concentration up to 4% wt was considered, with the aim of obtaining gels with a denser mesh size. This should confer the material the ability to resist longer in vivo and grant a longer retention of the encapsulated protein. A minimization of the calcium content was also investigated, to reduce possible side effects; the minimum required amount to obtain a gel, keeping constant all the other parameters, was found to be 4 mg/mL. As the mixing of the calcium and polymer solutions causes the immediate formation of a gel, it was not possible to measure the pH and the osmolality of the final formulation. Therefore, the osmolality of the polymer liquid solution was adjusted at the value of ~300 mOsm/kg using sucrose, 70 mg/mL. This addition caused an alteration in the gel formation, with the residual liquid phase not observed in the absence of sucrose. It was hypothesized that the sucrose interfered with the gel formation either by interacting with alginate or with calcium. Hence, the concentration of calcium was raised again at 10 mg/mL, leading to the formation of a gel with no residual liquids and precipitates.

The pH of the polymer solution was measured, obtaining the value of 7.0. The calcium solution showed a pH value of 5.3 and an osmolality of about 170 mOsm/kg.

The protein amount loaded in the polymer liquid solution was set at 54 μg/mL.

Finally, collagen type I was added to the polymer liquid solution, to improve the cell invasion capability of the gel, as reported in Rayatpisheh et al. (2011). Two different concentrations were tested, 1 and 2 μg/mL, according to the literature (Tsai et al., 1998).

At the end of this preliminary screening, four candidate formulations were selected. For all of them, the calcium solution was composed of calcium chloride 10 mg/mL in Milli-Q water, while the polymer solutions differ for both alginate and collagen type I content, as shown in Table 1.

All the experiments were performed using an easily available sodium alginate provided by Sigma-Aldrich. In the last part of the study a sodium alginate having the same characteristics but certified as Pharma Grade (PG) was purchased from FMC BioPolymer Keltone. The four candidate formulations were then re-prepared using PG alginate, and compared to the non-PG, obtaining comparable results in terms of visual inspection. Gels obtained with PG and non-PG alginate were also compared for their swelling and mechanical properties.

It is anticipated that although the experiments have been performed with calcium chloride, similar results would have been obtained with any further dicationic salts, such as magnesium salt, copper salt, or zinc salt.

Example 3: Preparation of Temperature-Responsive Gels (Chitosan)

Generalities

For the screening of chitosan formulations, the preparation of the polymer liquid solutions made use of three different chitosans: 95% deacetylation degree (DD) with high molecular weight (HMW), 95% DD with low MW (LMW) and 75% DD with high MW (HMW). Polymer liquid solutions were prepared by gradually adding the chitosan to a solution of acetic acid 0.1 N under vigorous stirring at either 5° C. or 25° C. The amount of polymer was calculated to have a final polymer concentration in the polymer liquid solution of 1% wt, 1.5% wt or 2% wt. Once the chitosan was completely solubilized, a solution of $KH_2PO_4$ at concentration of 10 mM, 100 mM or 500 mM in Milli-Q water was added under stirring, to have a final concentration in the polymer liquid solution of either 1 mM, 10 mM or 50 mM. Finally, a solution of β-glycerophosphate (β-GP) at a concentration of 20% wt in Milli-Q water was added in order to adjust the pH of the final liquid solution to a value of either 6.0, 6.5 or 7.0. The final concentration of β-GP in the polymer liquid solution ranged from 0.5% wt to 7% wt for the accepted formulations. It was not always possible to reach the desired pH value as too high an amount of β-GP was necessary, exceeding the target osmolality value of 350 mOsm/Kg or obtaining a gel already at room temperature. The polymer liquid solutions, when applicable, were then incubated at 37° C. up to gel formation. The osmolality of all the screened formulations was measured, discarding the formulations with an osmolality higher than 350 mOsm/Kg, i.e., formulations with final β-GP concentrations higher than 2.5% wt.

Preliminary Screening of Placebo Formulations

Temperature-responsive gels are based on a polymeric material that undergoes solution-gelation (sol-gel) transitions, changing the temperature of the local environment. Chitosan is reported to be able to undergo sol-gel transitions with temperature changes, but the process is highly influenced by the polymer molecular weight (MW), its deacetylation degree (DD), polymer concentration in solution, temperature, time and speed of mixing during the solubilization of the polymer, final pH of the solution and the presence of other excipients.

Therefore, an exhaustive screening of the different possible combinations was required. It is noteworthy that chitosan can be solubilized in water only at acidic pH. An increase in pH causes its aggregation and precipitation. A way to overcome this issue is the use of β-GP to increase the pH while maintaining the chitosan in solution.

The study was focused at the beginning on HMW chitosan with 75% DD. Several polymer liquid solutions were prepared in hydrochloric acid 0.1N, differing in final chitosan concentration from 1% wt to 2.5% wt and final β-GP concentration from 1.6% wt to 50% wt (1.6, 5, 5.6, 8, 30, 50%), and having different excipients, namely gelatine, glucosamine, hyaluronic acid, hydroxyethyl cellulose, carboxymethyl cellulose, trehalose, and different final pH values, from 6.0 to 7.0. These excipients were reported to play a role in the induction of gel formation (Cheng et al., 2010; Schuetz et al., 2008; Yan et al, 2010).

Only one of the screened formulations was able to form a gel at 37° C. after 5 minutes of incubation at 37° C., but the amount of β-GP was higher than 8% wt, reported in the literature as the limit above which cytotoxicity is recorded (Ahmadi et al., 2008). Therefore, all the following formulations were prepared considering that limitation. The screening continued, moving to a chitosan having a higher DD value. The first trials were based on LMW chitosan with 95% DD. The polymer solutions were prepared always in hydrochloric acid 0.1 N, solving the polymer under vigorous stirring at either 5° C. or 25° C.

After complete solubilization of the polymer, the other excipients were added, adding β-GP only at the end. β-GP was responsible for the increase in the pH value then, promoting the gelation process. The first trials were focused on formulations based only on chitosan and β-GP at different combinations of relative concentrations. It was observed that using high concentrations of chitosan (2% or 3% wt) and high concentrations of β-GP (8% wt), the formation of the gel occurred already at room temperature, and in some cases also at 5° C.

Decreasing the concentrations of either component, the formulation remained liquid, also after long incubation at 37° C. Only in one case was the formation of the gel registered, but after 2 hours of incubation at 37° C., this was too long a time for the purpose of this study. Therefore, the addition of an excipient was mandatory for improving the formulation. Hydroxyethyl cellulose (HEC) was selected as the most appropriate excipient and a further screening was carried out. During this evaluation, chitosan concentration ranged from 1.5% wt to 2% wt and starting HEC concentration was 0.5% wt, but in these conditions, the polymer solution became a gel even at room temperature during the addition of β-GP, if its concentration was above 1.8% wt. A liquid solution able to become a gel at 37° C. after 13 minutes of incubation was obtained with the following composition: 1.5% wt of chitosan, 0.5% wt of HEC and 1.7% wt of β-GP.

Optimization of the Formulation

In the attempt to improve this formulation, the following trials were made, maintaining the concentration of β-GP almost constant at the value of 1.65-1.7% wt. Chitosan concentration varied from 1.5% wt to 1.8% wt and the amount of HEC was gradually decreased to 0.1% wt.

Several candidate formulations were selected with this strategy. However, the investigation did not continue in this direction, as it was found that HEC excipient can contain a contaminant reported to be cytotoxic and, on the other hand, responsible for the gelation process modulation in the presence of chitosan (Hoemann et al., 2007). Other excipients tested in the previous experiments, such as gelatine or glucosamine, did not give positive results.

A final screening work was then started, using three kinds of chitosan polymer, differing in molecular weight and DD: HMW chitosan with 75% DD, HMW chitosan with 95% DD and LMW chitosan with 95% DD. The work was also planned on LMW chitosan with 85% DD, but the material was not available before the end of the study. In that work each chitosan was tested at three fixed concentrations, 1, 1.5 and 2% wt, and the polymer solutions were prepared in order to have final pH values of 6.0, 6.5 and 7.0. In order to reduce the amount of β-GP used to increase the pH value of the solution, the polymer was solved in acetic acid 0.1 N, instead of the HCl 0.1 N used in the previous experiments. The osmolality of the final solution was also monitored and kept below the value of ~350 mOsm/kg. Thus, the formulations that required too high an amount of β-GP to reach the desired pH, also leading to too high an osmolality value, were discarded. In these screening tests, the contribution of ionic strength was also studied, as it was reported that the presence of salts could give a positive contribution to the gelation process (Filion et al., 2007).

As sodium salts had to be avoided for possible interactions with the protein, $KH_2PO_4$ was chosen and added to the polymer solution at the final concentration of 1 mM, 10 mM or 50 mM. Chitosan with 75% DD gave no positive results and it was completely abandoned. Neither HMW chitosan with 95% DD gave positive results: chitosan concentrations higher than 1% wt required too high an amount of β-GP to reach the fixed pH values, exceeding the target osmolality value, and the formulations at 1% wt were not able to form a gel at 37° C. Two candidate formulations were selected with LMW chitosan having 95% DD, as they underwent sol-gel transition at 37° C., but the preparation of these polymer solutions was not completely reproducible. Indeed, it was observed that the time required to obtain a gel and the physical macroscopic characteristics of the polymer liquid solutions changed significantly, depending on the time spent to dissolve the polymer, the speed of mixing during the polymer dissolution and during the mixing of the excipients and, finally, the temperature and volume of the prepared solution.

This high variability in the results led to the decision to interrupt the study on this polymer.

Example 4: Gelation Time and Temperature

All the formulations studied in this work are planned to be used as in situ, forming gels. Therefore, an important requirement was a fast gelation time, both for ion- and temperature-responsive gels. It was indeed important to identify a formulation with good gelling properties but whose gelation process is neither too fast (to allow injection) nor too slow (not to risk to loose material). The gelation time was determined by a tilting test: the solutions were turned upside-down and the gel was considered formed when no flowing of liquid was observed.

Ion-Based Formulations

In the case of alginate-based formulations, the gelation process was influenced by the calcium solution concentration and the relative ratio between the calcium and alginate solutions. The gels were prepared in glass Petri dishes, adding the alginate solution first and then the calcium solution, trying to homogenize the two solutions as much as possible. If the amount of calcium chloride was not enough, no gel formation was observed, even after incubation at 37° C. for a long time. Increasing the amount of cross-linking agent (calcium) and adjusting the polymer solution: calcium solution ratio, a gel was formed almost instantaneously, as soon as the two solutions were mixed together. In some cases, a remaining liquid phase was observed. The time required for the total disappearance of the liquid after incubation at 37° C. was considered the gelation time.

The gelation time varied from 5 minutes to 2 hours, and, in some cases, the total disappearance of the liquid was not reached. The gelation was faster with polymer liquid solution at 4% wt concentration of alginate than 3% wt. The addition of collagen type I did not show any impact on the gelation time. The results are summarized in Table 2. The two candidate formulations at 4% wt alginate concentration of the polymer solution showed a gelation time of 5 minutes, while the two candidates with 3% wt polymer solution showed complete gelation in 15 minutes.

Importantly, when the gels were formed using a syringe connector that allowed for the contemporary injection of the two solutions, no remaining liquid phase was observed at any polymer concentration. In fact, the contextual injection of the two solutions allows for a faster and more homogeneous mixing of the two flows, leading to instantaneous gelation.

It is anticipated that although the experiments have been performed with calcium chloride, similar results would have been obtained with any further dicationic salts, such as magnesium salt, copper salt, or zinc salt.

Temperature-Based Formulations

Temperature-responsive gels were designed to be liquid at room temperature during the preparation and handling phase and become a gel after injection, that is, at 37° C. in physiological conditions. The test was carried out by incubating the different chitosan-based formulations at 5° C., 25° C. and 37° C. to monitor the gelling time as a function of temperature by tilting test. Results are summarized in Table 3.

Depending on the chitosan and β-GP concentrations, the behavior changed significantly. Using solutions too much concentrated in β-GP, the gelation occurred already at room temperature, during the preparation of the liquid solution. For this reason, it was important not only to optimize the formulation by changing the concentrations of the components, but also to dissolve and mix all the ingredients at 5° C. and then incubate the liquid solution at 37° C. After proper optimization, as described in Example 3, gel formation at 37° C. was obtained after 15 minutes, but it was found that the result was not reproducible. In particular, it was observed that the gelation time was influenced by the speed and duration of mixing required to dissolve the chitosan and mix it with the other components Example 5: Mechanical Properties Hydrogels are a group of semi-solid materials made of hydrophilic polymer networks with high water retention capacity. In general, hydrogels have mechanical features intermediate between viscous liquids and elastic solids (viscoelastic properties) (Anseth et al., 1996). It is of importance that their mechanical properties are determined and measured under conditions that resemble the target in vivo environment.

Dynamic mechanical analyses are able to characterize the viscoelastic behavior of hydrogels that reflects the combined viscous and elastic responses upon application of an oscillatory stress (typically shear). Viscoelastic materials are characterized by a storage modulus, G', and a loss or viscous modulus, G", that give a measure of the elastic and viscous contributions of the dynamic stress-strain behavior, respectively.

Hydrogels are defined, in rheological terms, as viscoelastic materials presenting G'>G" and both G' and G" independent of the oscillation frequency (Peppas et al., 2000). In particular, the higher the G', the higher the strength of the hydrogels, and the higher the difference between G' and G", the lower the liquid-like vs. solid-like behavior. In this section we report the investigation of the viscoelastic properties of alginate hydrogels using a rheometer equipped with a cone-plate geometry (see Examples section) by performing frequency sweep tests. In frequency sweep tests an oscillatory shear stress is applied in a range of frequencies (0.1-100 rad/sec). G' and G" are then plotted vs. frequency.

FIG. 1 shows the frequency sweep results relative to 3% wt alginate gels, with different collagen contents (0, 1, 2 μg/mL) in the alginate solution and different FGF-18 contents in the alginate solution (0, 54, 540 μg/mL). All samples were analyzed after 30 minutes of incubation at 37° C. after the addition of the calcium solution. Measurements with FGF-18 at 540 μg/mL in the alginate solution were made to investigate if a ten-fold higher protein concentration could impact the inner structure of the material.

Visibly, all samples showed the typical behavior of gels, showing G'>>G", both independent of the angular frequency. G' values are comprised for all samples between approximately 300 and 400 Pa. These differences in G' were not indicative of substantial differences in the elastic response of these materials. This means that the low concentration of collagen in the formulation (1 or 2 μg/mL) did not impact the mechanical properties of the gel at time zero. Anyway, it can promote a higher stability of the gel upon incubation, as it will be shown in the next section.

It is also important to notice that the presence of FGF-18 did not impact the mechanical properties of the material either at 54 or 540 μg/mL in alginate solution. In fact, no significant differences or trends could be identified between placebo and active gels at the two different protein concentrations. This is an important parameter since it allows for the formulation of FGF-18 at a wide range of concentrations of protein in alginate solution (0-540 μg/mL) without impairing the properties of the matrix.

Figure 2:
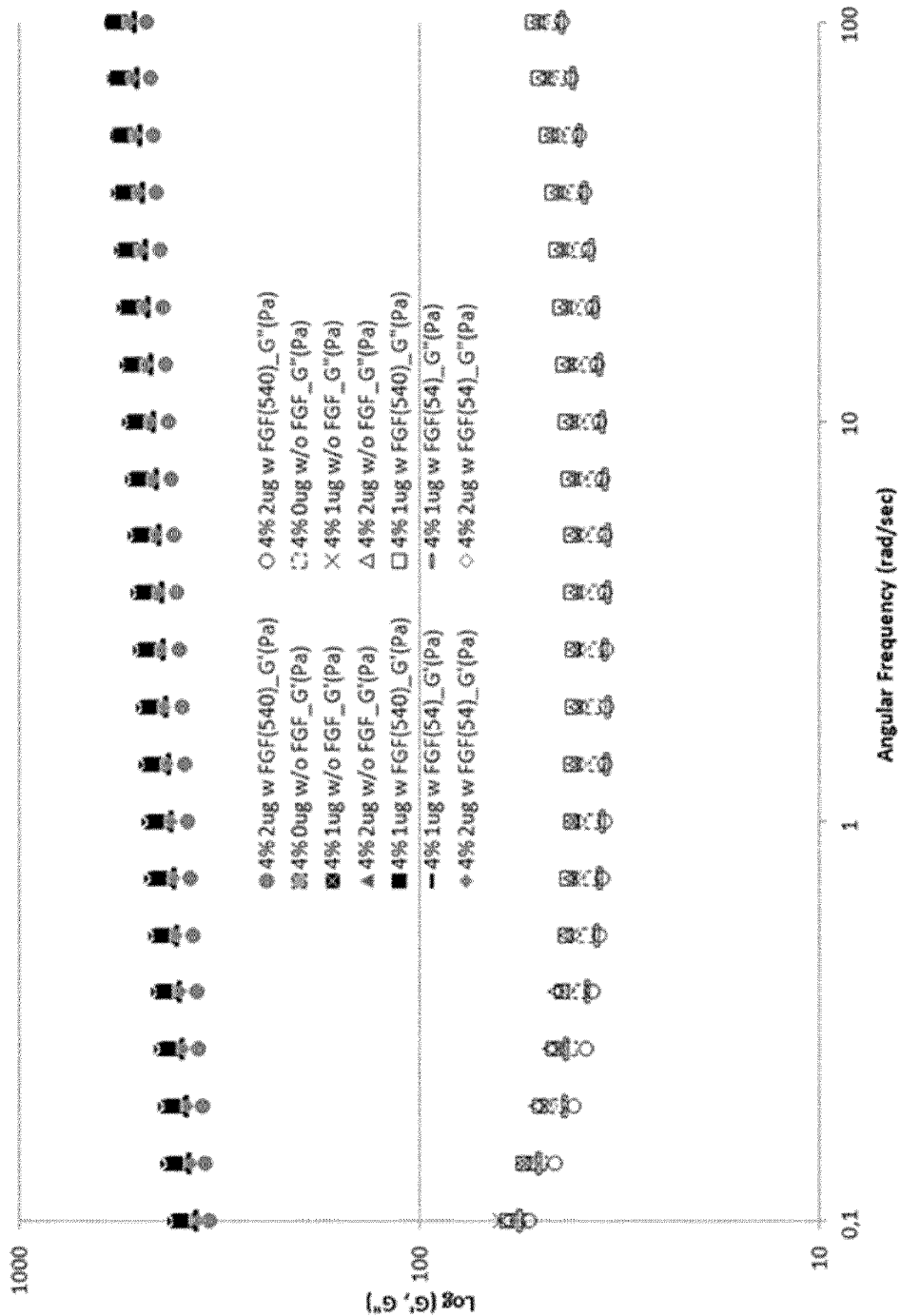
FIG. 2: Frequency sweep test performed on 4% wt alginate based gels: placebo (w/o FGF), with FGF-18 54 mcg/mL in the alginate solution (w FGF (54)) and with FGF-18 540 mcg/mL in the alginate solution (w FGF (540)).

FIG. 2 shows the results obtained on the 4% wt alginate candidates, the corresponding placebo and the placebo without collagen. Also in this case, all samples showed the typical behavior of gels with G'>>G", both independent of the angular frequency. Again, no impact of both collagen and FGF-18, either at 54 or 540 μg/mL in alginate solution, was visible, with all the G' values lying between approximately 380 and 500 Pa. It could be expected that a higher concentration of alginate should lead to a higher cross-linking density, hence an elastic modulus, G'. The recorded difference, instead, was not pronounced.

Anyway, it is important to stress the fact that the calcium solution added to both the 3% wt and the 4% wt alginate solutions was the same. This means that the 3% wt alginate solution was exposed to a higher relative concentration of cross-linker that could even lead to a denser mesh, depending on the rearrangements of the polymer chains in solution.

Figure 3:
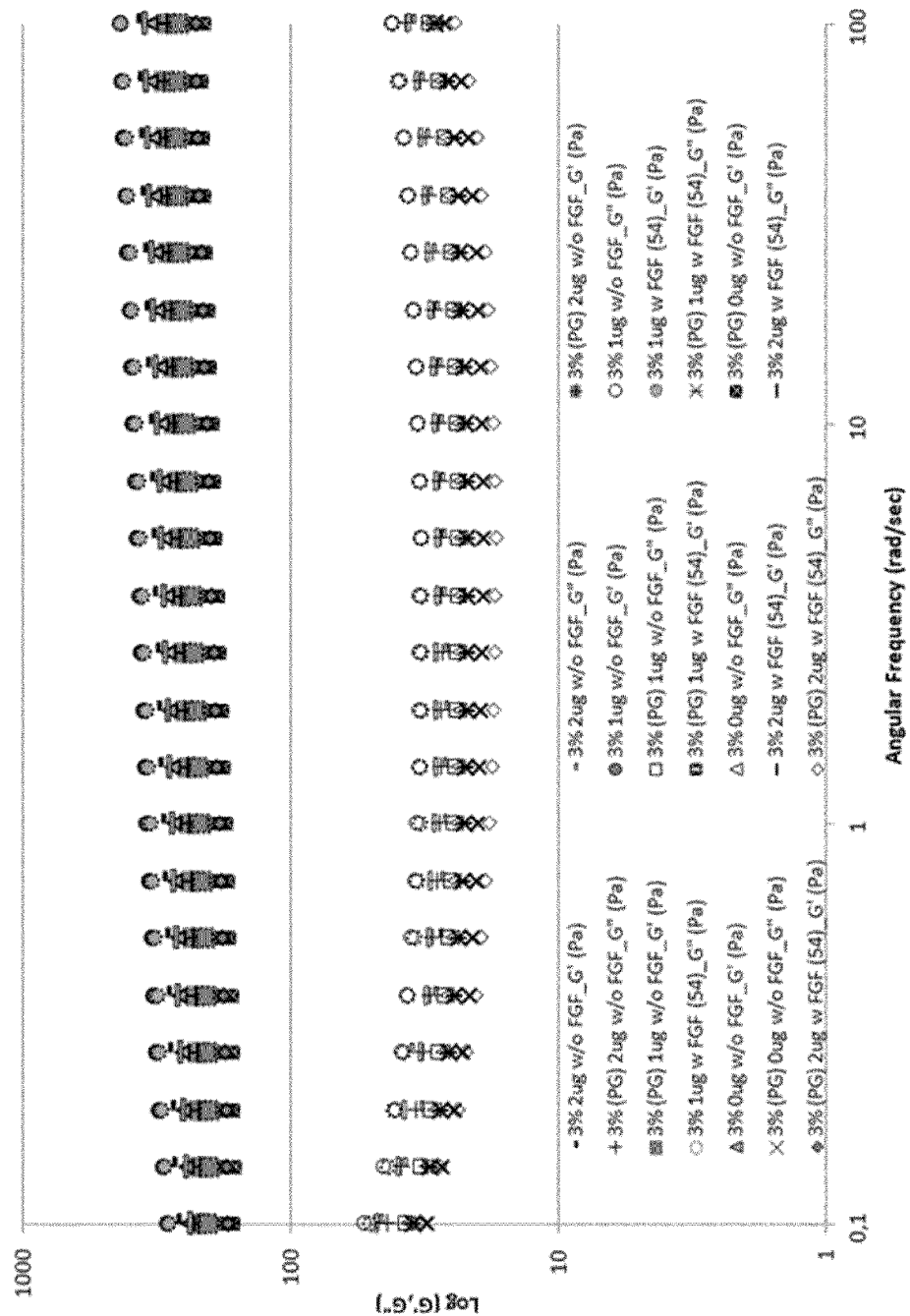
FIG. 3: Frequency sweep test performed on 3% wt PharmaGrade (PG) alginate based gels: placebo (w/o FGF), with FGF-18 54 mcg/mL in the alginate solution (w FGF (54)) and with FGF-18 540 mcg/mL in the alginate solution (w FGF (540)).
Figure 4:
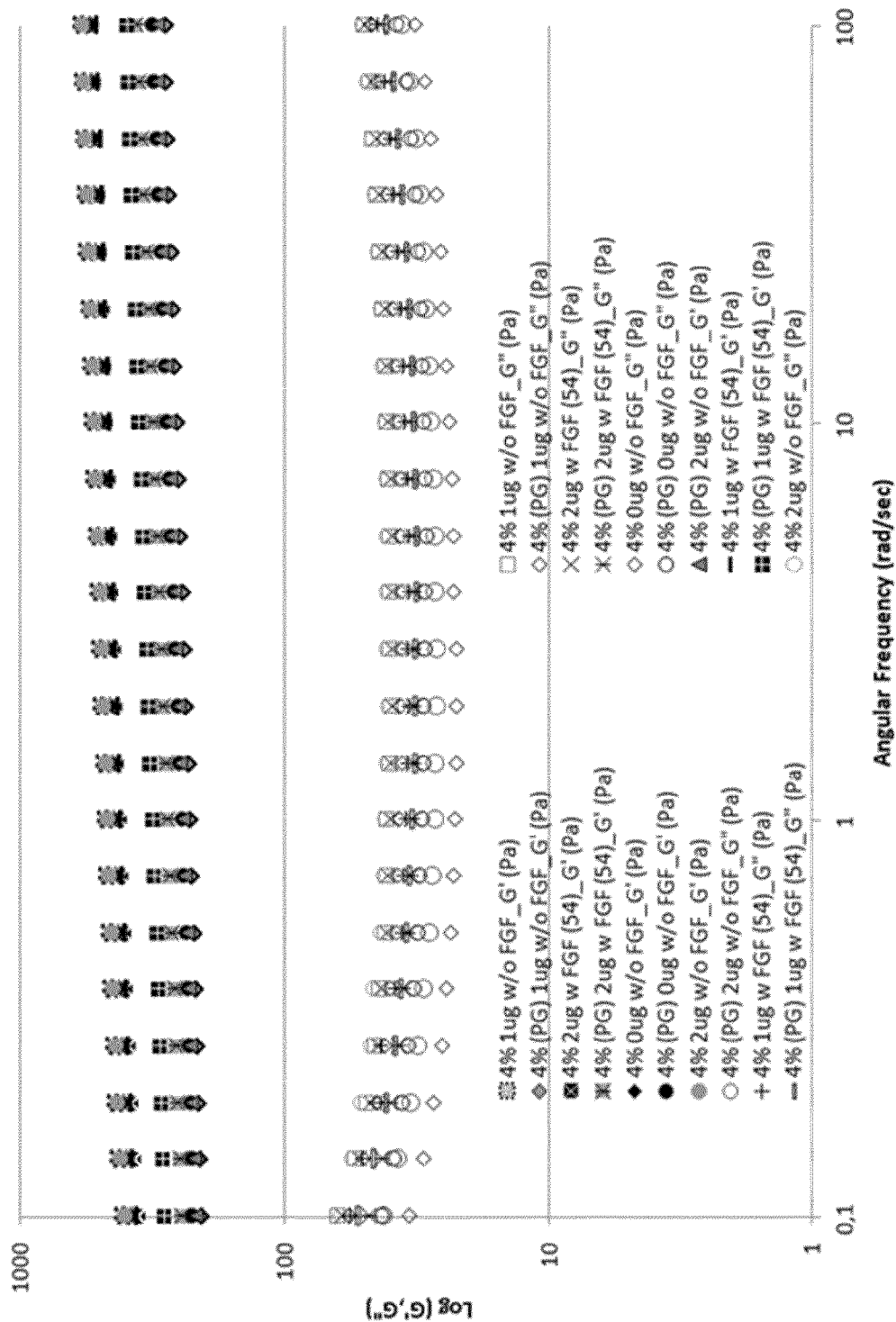
FIG. 4: Frequency sweep test performed on 4% wt PG-alginate based gels: placebo (w/o FGF), with FGF-18 54 mcg/mL in the alginate solution (w FGF (54)) and with FGF-18 540 mcg/mL in the alginate solution (w FGF (540)).

At the end of the study a Pharma Grade (PG) alginate was available. In order to make sure that the purity level of the alginate did not impact the structure of the gels, frequency sweep tests were also performed on PG alginate based gels. Results are shown in FIG. 3 and FIG. 4.

The results obtained for PG alginate were perfectly comparable to those obtained with non-PG alginate. The only difference was a slightly wider dispersion of results within both the 3% wt and the 4% wt gels. This could be due to a slight difference in the molecular weight distribution of the raw material, despite the fact that the technical sheets of the PG and the non-PG alginate report the same specs.

Anyway, again no particular trend or remarkable differences within the 3% wt and the 4% wt systems could be observed and the slightly higher G' values observed for the 4% wt systems was also confirmed with the PG raw material.

Example 6: Swelling Behavior

A typical parameter that has to be evaluated for hydrogel materials is their ability to swell or shrink in the presence of a liquid. The test was used to predict the behavior of the material once injected in vivo conditions, where it will be in contact with the physiological synovial fluid.

The study was carried out only on alginate-based gels prepared according to example 2, as chitosan formulations were discarded, as explained in Example 3. Thus, the four candidate alginate-based gels were incubated at 37° C. in contact with MSF and their behavior was monitored for 30 days (see "swelling behavior assay" in the Methods section).

Figure 5:
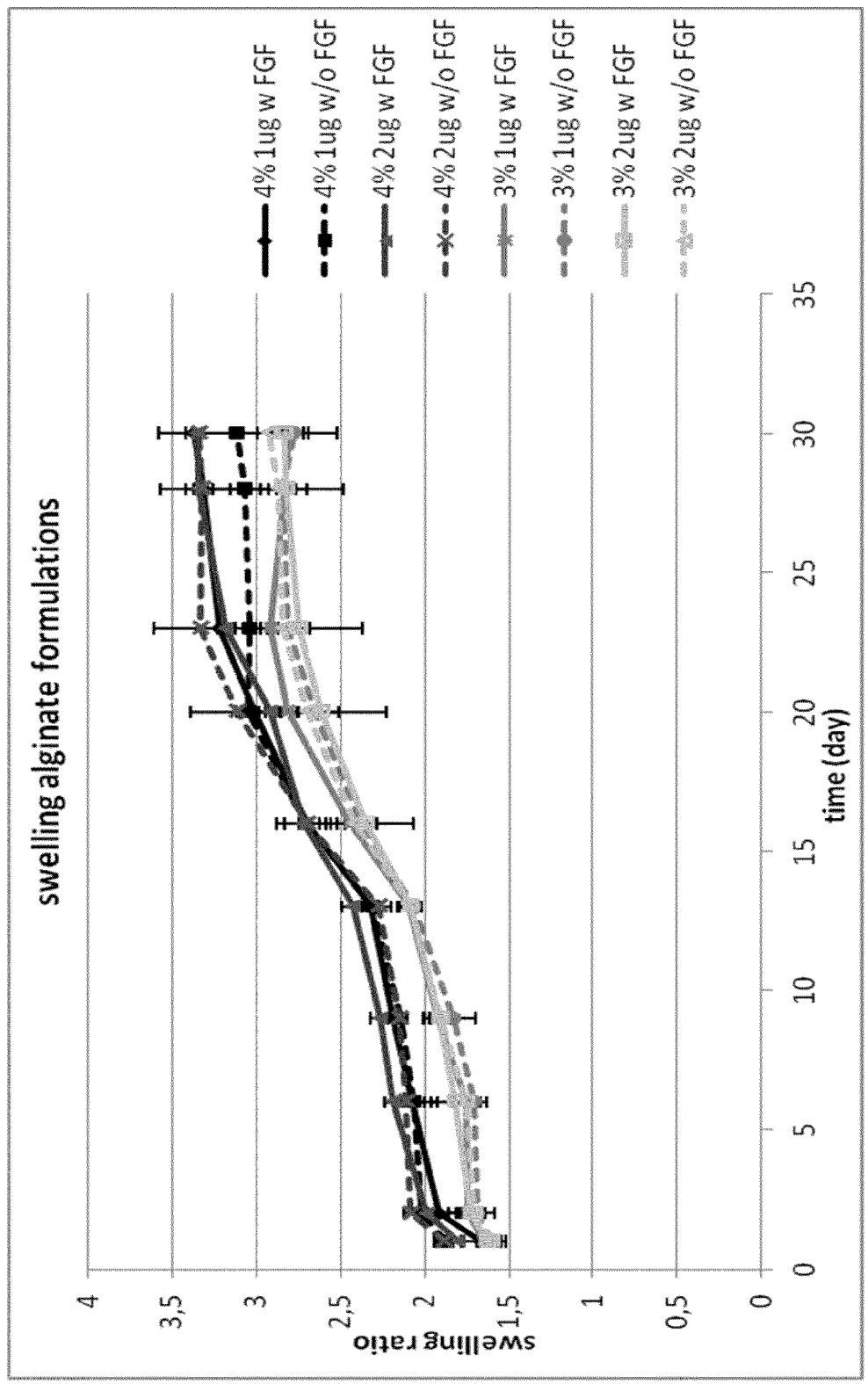
FIG. 5: Swelling ratio of candidate placebo (w/o FGF) and active (w FGF) alginate-based gels, prepared with non-PG sodium alginate.

In FIG. 5, the swelling behavior over 1 month for the four candidate alginate-based gels is reported both for placebo and active gels. As reference, the same gels without collagen type I were also tested, to investigate its effects on the gels' structural characteristics. These results are reported in FIG. 6. Both FIGS. 5 and 6 refer to non-Pharma Grade alginate (non-PG).

In both cases, the higher the concentration of alginate, the higher the swelling ratio. This behavior is apparently in contrast with the results obtained by rheological measurements. In particular, higher polymer concentrations should form a denser network that, in turn, is usually associated with a lower ability to absorb aqueous solutions. It has to be considered that the concentration of $Ca^{2+}$ was kept constant, and, therefore, the ratio between polymer and cross-linking agent varied by varying the polymer concentration. A lower availability of cross-linking agent might lead to the formation of areas where the polymer is not cross-linked, letting water permeate easily. This could explain the differences in the swelling ratios between candidates at 3% wt and 4% wt alginate and was confirmed by SEM pictures shown in the next section.

Figure 6:
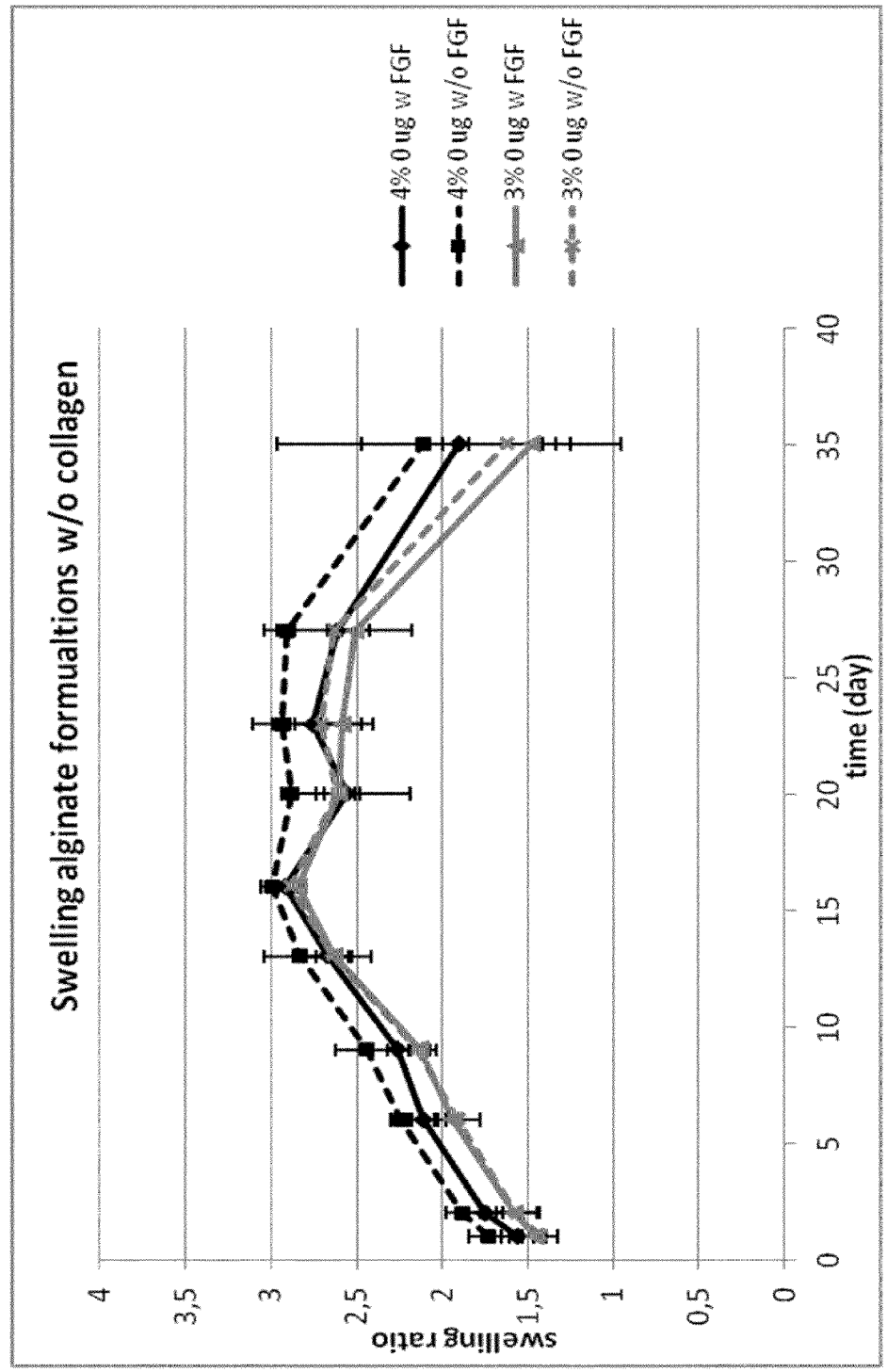
FIG. 6: Swelling ratio of placebo (w/o FGF) and active (w FGF) alginate-based gels without collagen type I, prepared with non-PG sodium alginate.

A comparison between FIG. 5 and FIG. 6 shows that the presence of collagen type I has an impact on swelling behavior, especially in terms of kinetics. While in the absence of collagen all the gels increased their weight monotonically for about 15 days, and then reached a plateau, the presence of collagen, independently of the concentration, led to a sinusoidal trend. The first plateau reached after 2 days in the presence of collagen indicates an equilibrium swelling corresponding to the maximum amount of water that the gel can retain. This value was lower than the corresponding swelling ratio values in the absence of collagen, suggesting a tighter structure of the gels, as expected after the addition of collagen. The subsequent swelling ratio increase after 15 days of incubation indicated the start of a network erosion phenomenon, with consequent MSF solution absorption as the mesh became looser. A second plateau was then reached after 24 days and was maintained until the end of the observation period of 1 month. The further erosion of the network was expected to lead to a further weight, hence swelling ratio, increase followed by a decrease until complete erosion has occurred. In the absence of collagen (FIG. 6), a continuous swelling ratio increase was observed followed by a slow erosion. This behavior was likely to be related to contemporary erosion and water uptake due to the looser structure of the gels.

As mentioned, no differences were recorded between gels obtained with either 1 or 2 µg/mL of collagen type I in the polymer solution.

Figure 7:
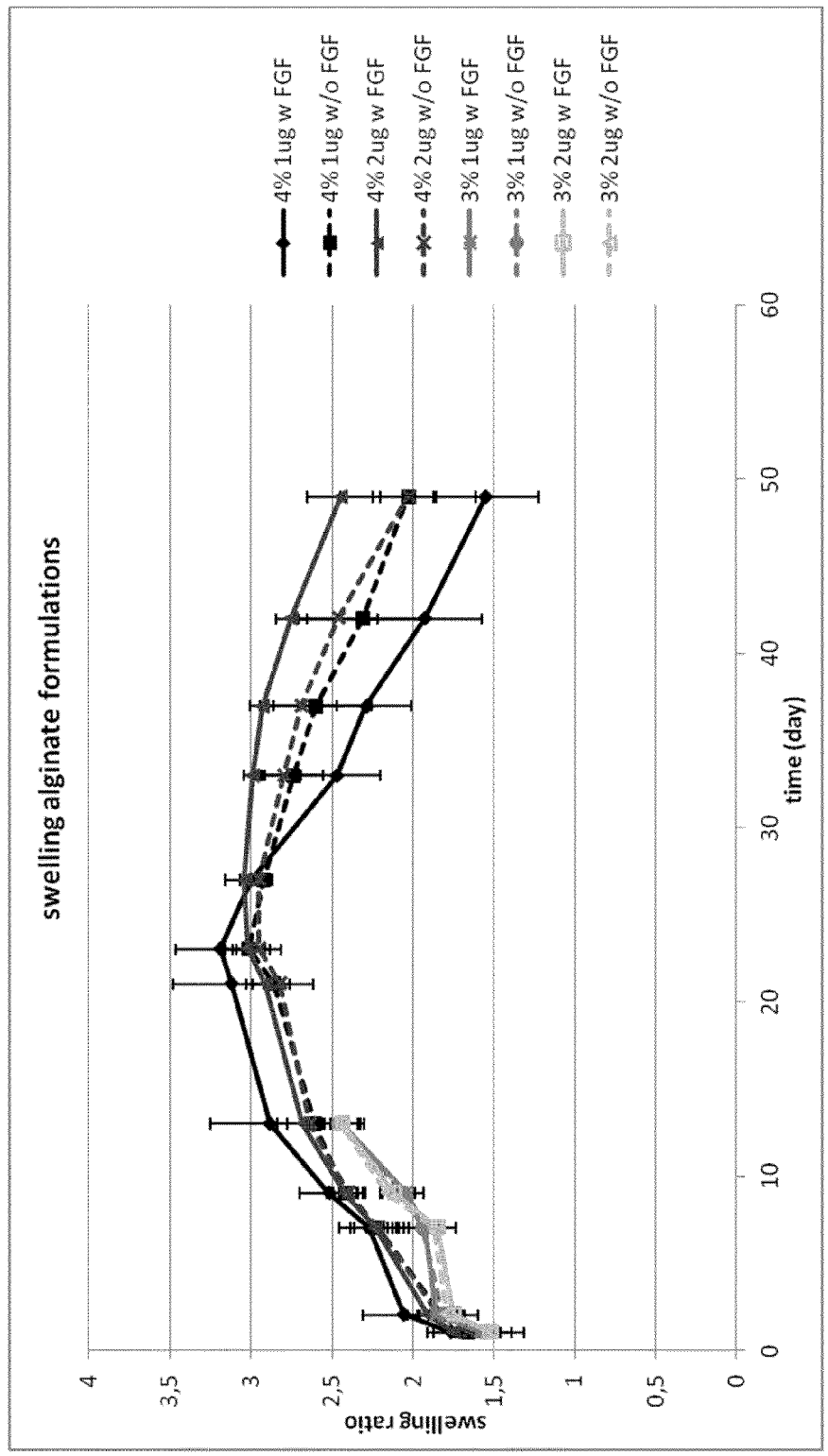
FIG. 7: Swelling degree of candidate placebo (w/o FGF) and active (w FGF) alginate-based gels, prepared with PG sodium alginate.

Interestingly, no differences were observed, either, between placebo and active gels. This suggested that a final 36 µg/mL concentration of FGF-18 in the gels did not impact the inner structure of the material. The experiments were repeated with the same formulations, this time prepared using PG alginate, and the results are reported in FIG. 7.

Visibly, the results are perfectly comparable to those obtained with non-PG alginate, the only difference being a lower deviation between the 3% wt and 4% wt alginate gels' swelling ratios compared to the non-PG material. The experiment was conducted up to 50 days for the 4% wt gels that show the expected behavior, i.e., a weight decrease after the second plateau indicating a slow continuous erosion.

Example 7: Scanning Electron Microscopy (SEM) Analysis

SEM images were taken to investigate the microscopic structure of the material once the gel is formed. The analysis was carried out on gels freshly prepared and then lyophilized.

Figure 8:
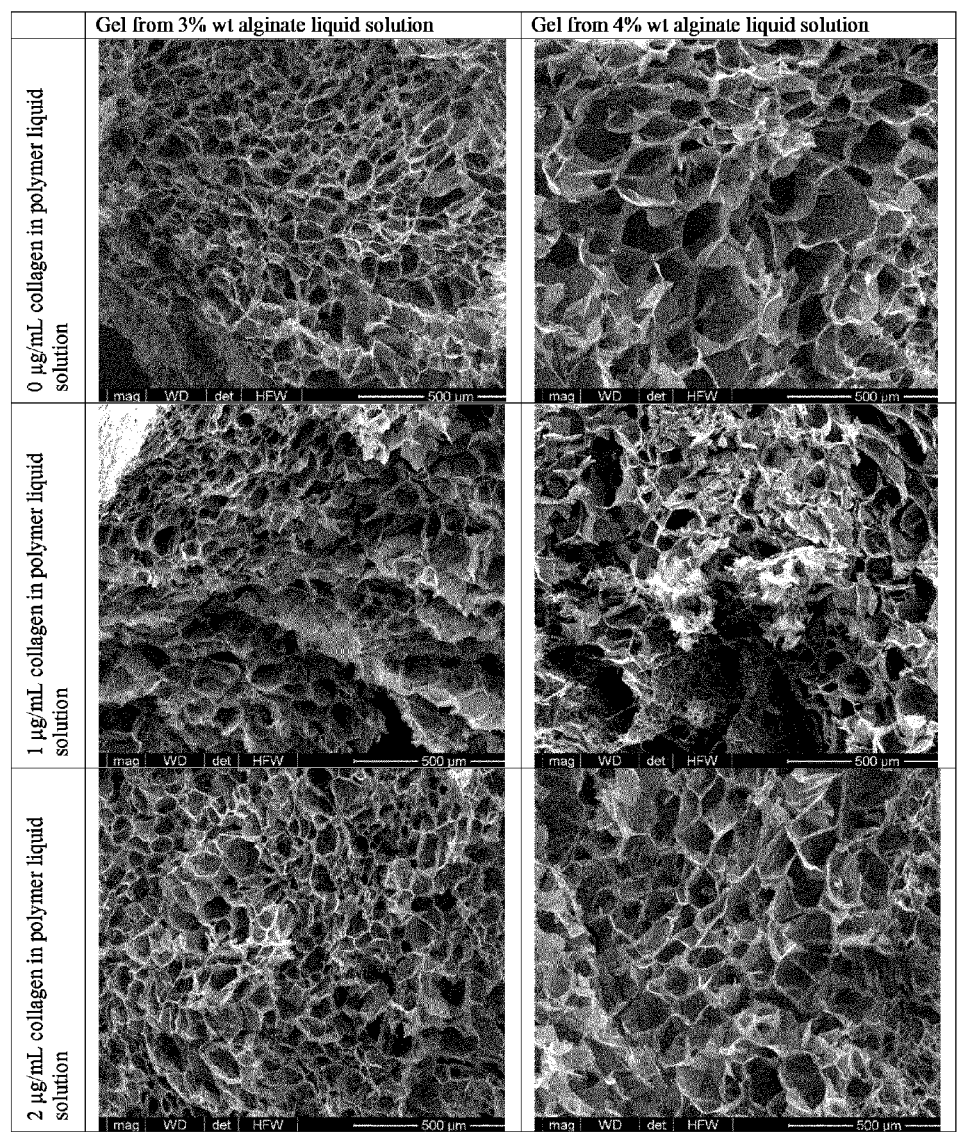
FIG. 8: SEM Images (100×) of alginate-based gels from polymer liquid solutions at 3% wt or 4% wt, containing 0, 1 or 2 mcg/mL of collagen type I and FGF-18 54 mcg/mL.

The comparison of samples with and without collagen type I, at both polymer concentrations, presented in FIG. 8, evidenced that collagen had no significant effect in the microporosity of the 3% wt alginate gels and only a slight effect on the 4% wt which showed a slightly tighter structure when added with collagen, either 1 or 2 µg/mL.

From the micrographs, a difference in the porosity is evident between the two materials, the 4% wt alginate gel showing bigger cavities than the 3% wt. This can be explained, again, by the fact that the relative concentration of cross-linker in the 3% wt alginate formulation was higher than in the case of the 4% wt. This could induce a denser structure in the 3% wt gels. These images were in line with the swelling results and in apparent contradiction of the mechanical properties analysis. In fact, the bigger cavities present in the 4% wt gels explain the higher swelling degree observed compared to the 3% wt. On the other hand, the slightly higher elastic modulus, G', observed for the 4% wt can be explained by the presence of non-cross-linked or loosely cross-linked alginate chains in the big pores, that contributed, anyway, to G'.

Example 8: In Vitro Release Study

The in vitro release study was performed contextually to the swelling test, collecting the receiving phase of each well at each time point considered. All the samples coming from active alginate-based gels were analyzed by RP-HPLC. In addition, selected samples were also analyzed by Biacore, a more specific and sensitive analytical method, in the attempt to find confirmation of the results obtained from RP-HPLC.

Before starting with this experiment, the feasibility of the test was evaluated. In particular, the recovery of FGF-18 in the well plate system was investigated. In fact, from previous studies it is known that the protein tends to stick onto different plastic materials, such as polystyrene, and membranes. The recovery of a known amount of free FGF-18 was evaluated in different experimental conditions. Possible positive effects of the presence of F68 surfactant and/or pre-treatment of the wells with a concentrated solution of HSA or FGF-18 were tested. The experiment was performed by adding an FGF-18 solution at a concentration of 500 µg/mL to the inserts and to each well in the following solutions:

a) solution of 1% wt of HSA in PBS,
b) solution of HSA 1% wt in PBS+F68,
c) and d) the same as a) and b), but pre-treating the well with a concentrated solution of HSA, and
e) and f) the same as a) and b) but pre-treating the well with concentrated bulk of FGF-18.

After incubation at 37° C. for 16 hours, the phases in the wells and in the baskets were analyzed and the resulting recovery was around 75%, for all the samples. Thus, none of the strategies to improve the tests had a significant positive effect, as the recovery was comparable. The in vitro release was then carried out using a solution of HSA 1% wt in PBS with F68 0.25 g/L as receiving phase.

Experiments were carried out keeping the gels under incubation for 30 days. FGF-18 was not detected in any of the collected fractions, either by HPLC or Biacore. This suggests that protein is entrapped in the gel matrix for the observation period.

These results can be expected taking into account the strong interaction occurring between FGF-18 and alginate. In fact, considering the structure of the two molecules, both ionic and hydrophobic interactions are likely to occur. In addition, FGF-18 is a heparin-binding protein showing high-energy secondary interactions with heparin. Alginate is a natural carbohydrate with a molecular structure similar to heparin, and hence, very strong secondary interactions between the two macromolecules are very likely to take place.

To confirm this, separation experiments were carried out, showing that only HIC or heparin-coated chromatographic columns were able to separate FGF-18 from alginate.

Example 9: In Vitro Cell Invasion Assay

The administration of FGF-18 in formulations able to create a 3D structure after injection, as in the case of alginate-based hydrogels, has the purpose of localizing the active molecule (API) in the site of injection. At the same time, the formulation creates a scaffold in which the growing cartilage could be anchored. For this reason, an important requirement for the selected alginate-based gel is the compatibility of the material with chondrocyte cells and its capability of being invaded by the cells. Therefore, a study was carried out on cell invasion, cytotoxicity and chemotaxis properties of alternative formulations based on in situ forming hydrogels loaded with FGF-18.

In vitro cell invasion assay was performed with two chondrosarcoma cell lines, the ATDC5 murine chondrogenic cell line and CRL-7891 human chondrosarcoma cell line, commonly used to study chondrocyte behavior. The experiments were performed on gels prepared from alginate liquid solutions at 3% wt or 4% wt containing 0, 1 or 2 µg/mL of collagen Type I and 54 µg/mL of FGF-18.

Cell invasion was monitored after 24, 48, 72 and 144 hours of incubation. The gel was removed from the well and a slice was cut, placed on a glass and observed on an Axiovert 200 microscope with Zeiss A-Plan 10×/0.25 object glass. This way, it was possible to analyze a gel section and localize the cells at different level of penetration depth. Pictures were captured and processed by AxioVision 4.2 software. Some samples were also analyzed by confocal laser scanning microscopy (CLSM), using an FV10 Olympus, available for a limited period for demo use. For these experiments, the gels were treated with a solution of Rhodamine B in PBS at a concentration of 0.2 µg/mL, added to the medium in the well 1 hour before the analysis. Rhodamine B was used to stain the cells, which were then visualized exciting the samples with a laser at 553 nm.

Cell invasion in alginate-based gels with polymer liquid solution at 3% wt or 4% wt, with or without collagen, was monitored at 24, 48, 72 and 144 hours. At each time point, a gel slice was cut to observe the section of the gel (data not shown). The first observation was a good compatibility of the formulations with the cells, as alginate-based gels seemed to be non-toxic for both cell lines, which showed comparable behavior even deriving from different species (mouse and human).

In formulations with alginate gels at 4% wt, more cells and cell clusters were found inside the gel.

Figure 9:
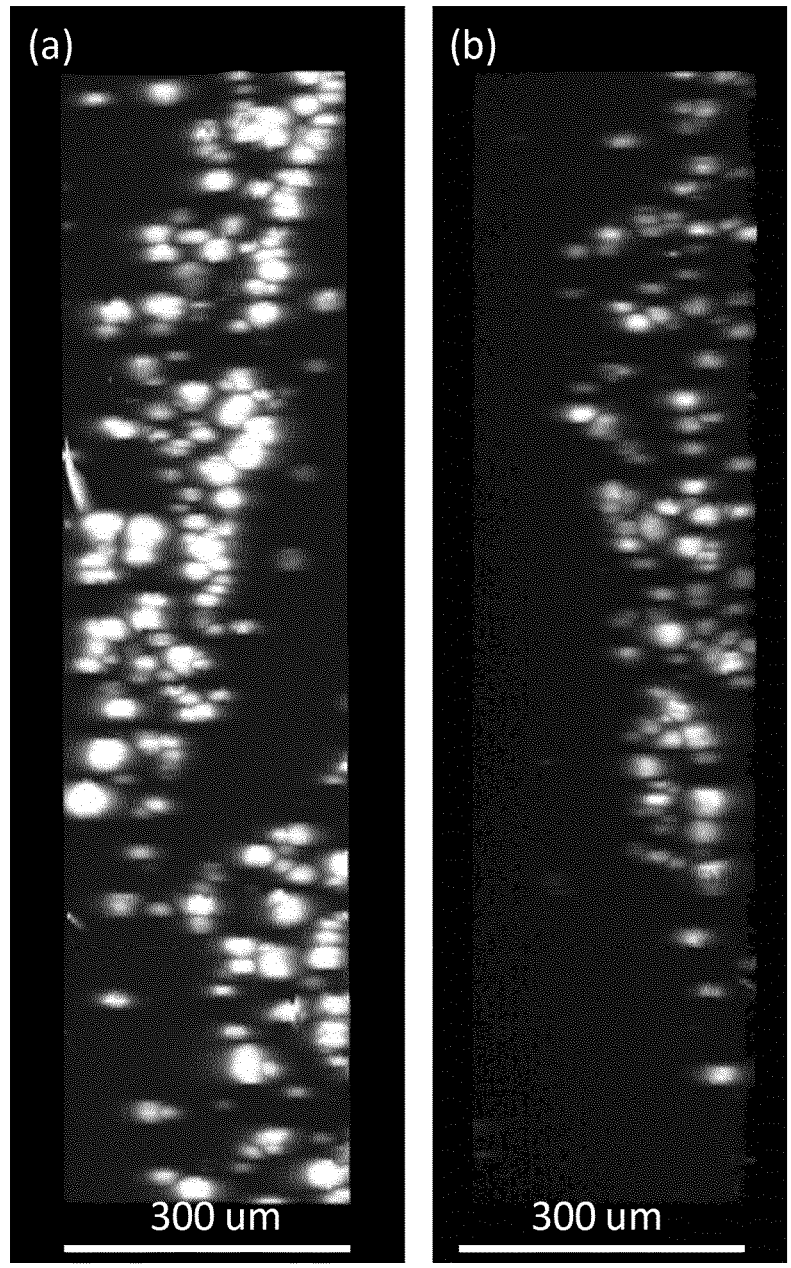
FIG. 9: Section view of a 3D image acquired by CLSM for (a) alginate-based gel with 2 μg/mL collagen type I after incubation with HTB94 cells for 72 h and (b) alginate-based gel without collagen after incubation HTB94 cells for 144 h. In white, HTB94 cells labeled with Rhodamine B. Right hand: top of the gel; left hand: bottom of the gel.

A different behavior can be observed for alginate gels at 4% wt containing 2 µg/mL collagen type I. More cells invaded the gel compared to the other formulations. Furthermore, cells did not create clusters, but appeared well-distributed along the gel as single and well-separated cells. Their aspect seemed to reveal that they were in healthy conditions. Finally, it was observed that they penetrated into the gel matrix over time. Comparing the gel at 4% wt, with 2 µg/mL and without collagen, it was observed that the invasion was faster and more homogeneous in the presence of collagen (see FIG. 9). The analysis carried out by CLSM confirmed the ability of cells to invade the gel matrix.

Example 10: Ex Vivo Test in an Animal Model

The therapy based on these alginate formulations can be coupled to microfracture strategy. Thus, to prove the compatibility of the gels with this technique, a preliminary study on an ex-vivo animal model was required and for that purpose a cow knee was used.

Experiments were performed on the 4% wt alginate with 2 µg/mL collagen type I candidate gel. This gel was selected from among the other candidates as it showed the most promising results in terms of cell invasion, as shown above.

Holes were made on both the upper part of the shinbone and the lower part of the thighbone, having the same dimension expected for a microfracture surgery (1 cm depth×4 mm diameter). Holes were then filled with the candidate gel, injected with a syringe connector mixing the alginate solution and the calcium solution, respectively, at the time of injection. This allowed to obtain instantaneously a homogenous gel, without any dripping phenomena. The injections were performed both in upright and upsidedown positions, confirming that in both cases the gel remained inside the hole and no dripping of material was observed. The joint was also submitted to shaking and rapid movements, proving that the gel was well fixed inside the holes and no loss of material was observed. The joint with the injected gel was then evaluated after 2 hours incubation at 37° C.; the gel still filled the entire hole and, once removed, it appeared slightly red-colored, indicating that the blood coming out from the fracture was absorbed by the gel.

These preliminary results suggested the feasibility of the alginate formulation in the microfracture strategy.

Example 11: In Vitro Bioassay

Figure 10:
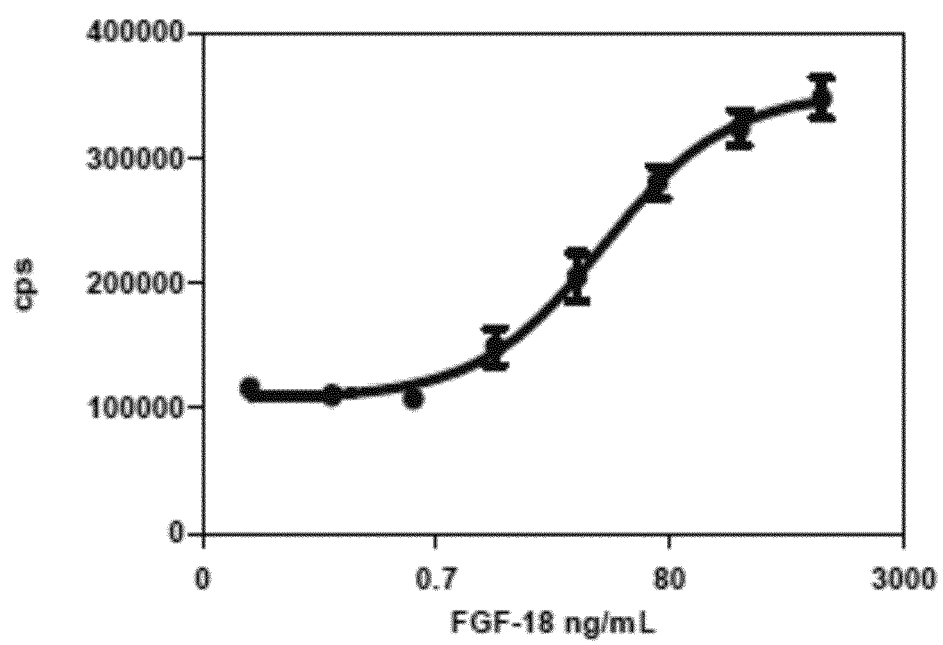
FIG. 10: FGF-18 bioassay in 4% wt alginate gel with 2 mcg/mL collagen type I.

The cell proliferation assay, conducted as described in the Methods section, showed that FGF-18 entrapped in the gel is bioactive with a clear dose-response curve, as shown in FIG. 10.

Conclusion

Ion-responsive gels were obtained from sodium alginate upon addition of calcium chloride as a cross-linking agent, while thermo-responsive gels were obtained from chitosan with the addition of β-GP to adjust the pH without any precipitation of the polymer.

Formulations based on either alginate or chitosan were tested at different polymer concentrations and the addition of other excipients was considered to adjust the pH and the osmolality of the formulations and, in some cases, favour the gelation process.

Gelling time results showed that alginate-based gels presented an extremely fast and reproducible gelation compared to chitosan. Thus, alginate gels were selected for further development.

Four candidate gel formulations were selected for characterization in terms of mechanical properties, swelling, in vitro release and cell invasion, formed by the addition of a calcium chloride 10 mg/mL solution to an alginate solution containing either 3% or 4% wt alginate, 1 or 2 µg/mL collagen type I, sucrose 70 mg/mL and FGF-18 54 µg/mL. The alginate solution volume to calcium volume ratio was 2:1.

The mechanical properties of the candidate gels were not impacted by the collagen concentration or the FGF-18 concentration at least up to 540 µg/mL. This is an important goal since the target concentration for FGF-18 in the hydrogel is still not determined, allowing for the possibility of formulating FGF-18 in these matrices in a wide range of concentrations without impairing the characteristics of the final gel. No major differences were observed in the elastic modulus, G', of the 3% wt and the 4% wt alginate gels, all presenting values comprised between approximately 300 and 500 Pa, the higher values being presented by the 4% wt gels.

All the candidate gels showed the same swelling profiles, indicating similar hydration and degradation processes. The only difference was in the absolute values, slightly higher for the 4% wt alginate gel. This result is in agreement with SEM micrographs that evidenced a higher dimension of pores for these gels.

After 15 days of incubation at 37° C. in mock synovial fluid all candidates showed a first degradation process indicated by a weight increase. In fact, the initial degradation of the network usually leads to a looser structure that can, hence, accommodate higher amounts of water. After 1 month, the continuous network degradation leads to the start of a macroscopic gel erosion, indicated by a slow weight loss. By the way, after 50 days of observation the gels are still not completely eroded, as indicated by the presence of some gel within the porous baskets (swelling ratio value at 50 days) (Lo Presti, C. et al., 2011; Dang et al., 2011).

A cell invasion assay was developed. The gel formulation showing the most promising cell invasion results contained alginate 4% wt and collagen 2 µg/mL. This formulation, then, was selected for an ex-vivo experiment on the adhesion properties of the gel. These ex-vivo experiments, carried out on a cow joint, showed that the candidate alginate gel can be injected, using a double injector for the alginate and calcium solutions, either in an upward or upside-down direction without any dripping. Furthermore, the gel was shown to perfectly fill and adhere to the cartilage holes mimicking the microfracture situation (data not shown).

Cell proliferation assays showed that FGF-18 entrapped in the gel is bioactive with a clear dose-response curve. As after 50 days of observation the gels are still not completely degraded and as the in vitro release experiments did not show any evidence of FGF-18 released in the mock synovial fluid, that suggests that FGF-18 will stay in the gel and thus will probably be more efficient in the long term at acting on the cells that have migrated in the gel. These results are thus promising.

Example 12: Freeze-Dried Formulation

After preparation of the polymer liquid solution containing FGF-18, sugar (sucrose) and collagen type I (see example 2), the solution was distributed in vials. Each vial (10 ml Fiolax Clear 45×24, SCHOTT forma vitrum) was filled with 2 ml of polymer liquid solution. All filled vials were submitted to the lyophilization process. In detail, the process foreseen the following steps:
  Cooling phase from 25° C. to −40° C. during 1 hour, where the freezing of the product starts;
  Freezing phase at −40° C. during 4 hours, where the product is kept frozen;
  Vacuum phase, with drastic decrease of pressure up to vacuum;
  First drying phase, with temperature going from −40° C. to −10° C. during 30 minutes and then staying at −10° C. during 10 hours;
  Second drying phase, with temperature going from −10° C. to 21° C. during 30 minutes and then staying at 21° C. during 34 hours; and
  Third drying phase, with temperature going from 21° C. to 37° C. during 16 minutes and then staying at 37° C. during 20 hours.

After the lyophilization process was finished, vials were closed with stoppers and stored at 2-8° C.

The freeze-dried product has to be reconstituted before using for the injection. It has to be equilibrated at room temperature, then 2 ml of WFI (water for injection) is injected into the vial, that was then swirled and moved to facilitate the reconstitution of the cake. The system is allowed to dissolve and homogenized during 30 minutes, before it becomes ready for injection.

Figure 12:
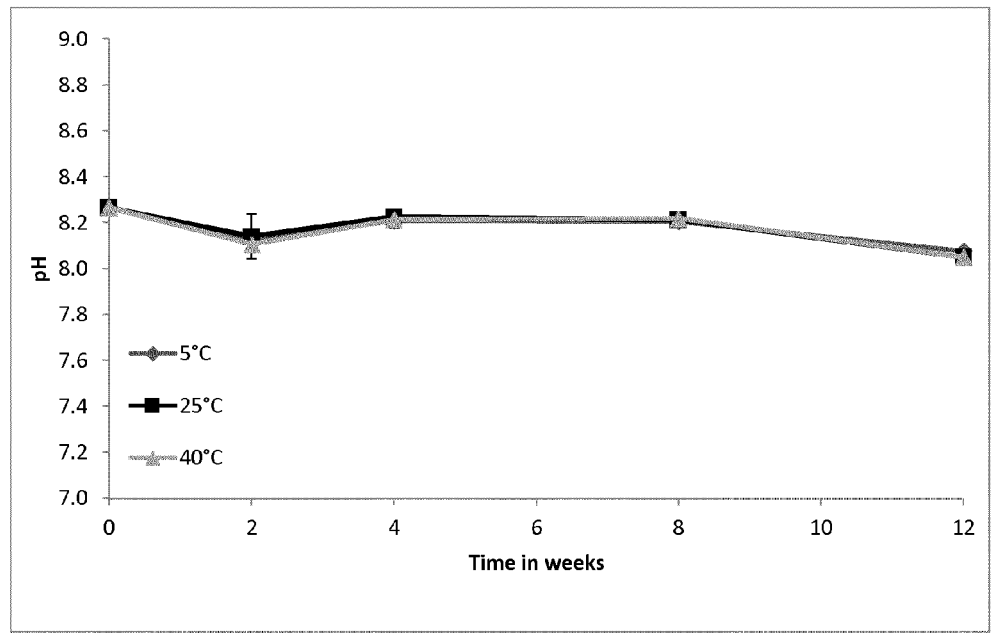
FIG. 12: pH variation of the freeze-dried (FD) formulation over time in 3-month stability in normal storage conditions (5° C.), accelerated conditions (25° C.) and stressed conditions (40° C.).

The freeze-dried formulation was then submitted to a 3-month stability study at 3 different temperatures: the normal storage conditions at 5° C., at 25° C. to perform accelerated stability and at stressed conditions of 40° C. The analysis were carried out at time 0, 2, 4, 8 and 12 weeks, after reconstitution of the samples with 2 ml of water. The following parameters were followed:
  pH
  Moisture content
  FGF-18 content
  Alginate content
  Alginate MW distribution
  Viscosity
  Mechanical properties
  Cell invasion capability
  Below are the main results up to 12 weeks.
  pH:

No significant variations in the pH value of the formulation were registered over the time of incubation at all three of the different temperatures. The pH of FD formulation is higher than the liquid one (most likely due to the filtration and lyophilization process to which it was subjected), but it did not change over time. The data presented in FIG. 12 suggested that the formulation is stable under normal storage conditions for up to 12 weeks.

Figure 13:
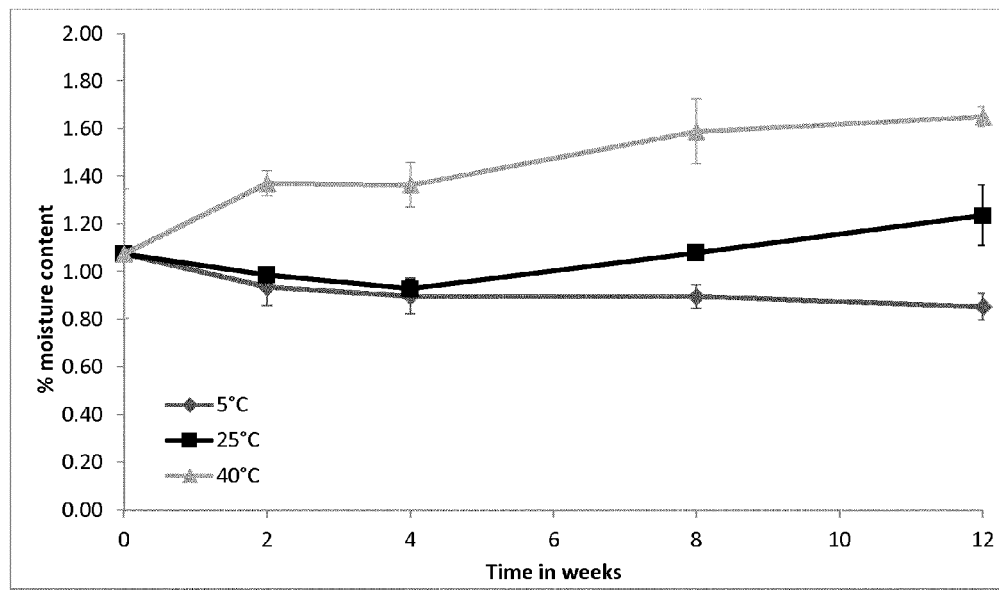
FIG. 13: % of moisture content variation of the freeze-dried (FD) formulation over time in 3-month stability in normal storage conditions (5° C.), accelerated conditions (25° C.) and stressed conditions (40° C.).

Moisture Content:

Residual moisture content was always inside the acceptance criteria (3%). The value was constant for the formulation stored at 2-8° C., while it slightly increased over time at 25° C. after 12 weeks of incubation, and even more at 40° C. already after 2 weeks, as expected. The data (see FIG. 13) suggested that the formulation is stable under normal storage conditions for up to 12 weeks.

Figure 14:
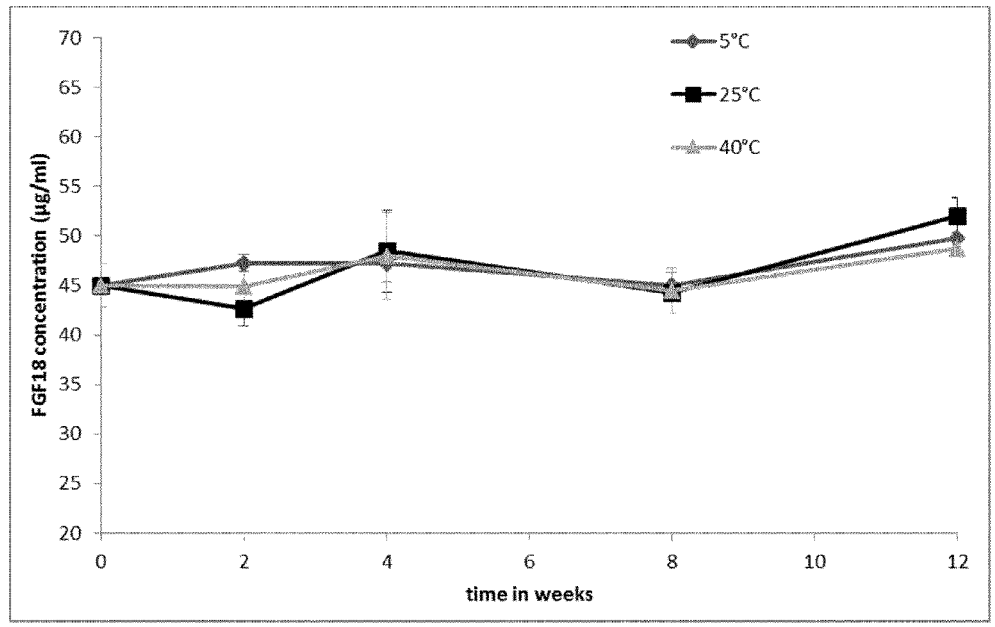
FIG. 14: FGF-18 content variation of the freeze-dried (FD) formulation over time in 3-month stability in normal storage conditions (5° C.), accelerated conditions (25° C.) and stressed conditions (40° C.).

FGF-18 Content:

No significant variation in the FGF-18 content was observed in the formulation over time at all three of the different temperatures, with total content slightly lower than the target concentration of 54 µg/ml, most likely due to loss of material during the different manufacturing steps, and in particular during filtration. The differences observed at the different time points were most likely due to the variability of the method, still under development, to the fact that the amount of the FGF-18 was close to the limit of detection of the method, and also to the variability of the vial contents, as proved also by the significant STD DEV of the results; indeed, the high viscosity of the solution did not allow for a well precise filling volume operated at lab scale. In general, the data suggested that the formulation is stable under normal storage conditions for up to 12 weeks (see FIG. 14).

Alginate Content:

No significant changes were observed in the alginate content over time at all three of the different temperatures.

Figure 15:
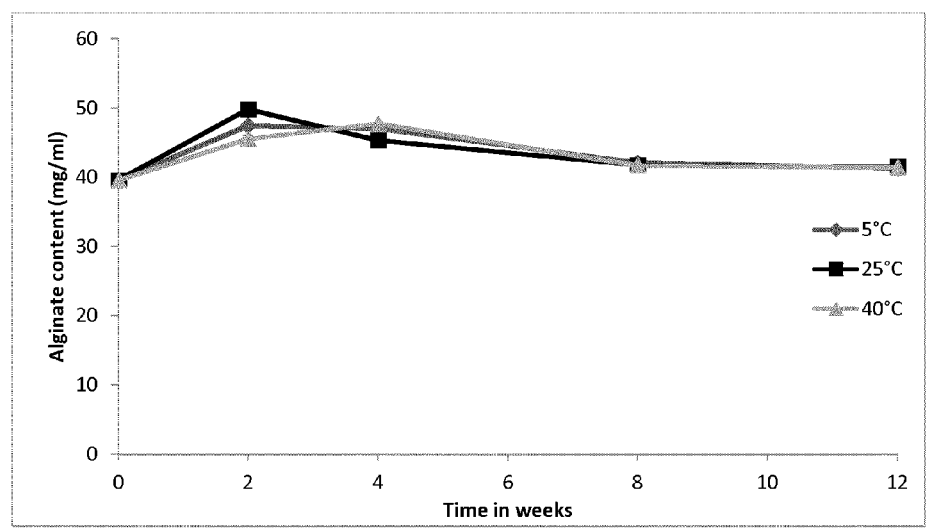
FIG. 15: alginate content variation of the freeze-dried (FD) formulation over time in 3-month stability in normal storage conditions (5° C.), accelerated conditions (25° C.) and stressed conditions (40° C.).

The variations observed were most likely due to variability of the method, still under development, and to the variability of the vial contents, as the viscosity of the solution did not allow for a well precise filling process at lab scale. The data, as per FIG. 15, suggested that the formulation is stable under normal storage conditions for up to 12 weeks.

Alginate MW Distribution:

No changes were observed in the chromatographic profiles, and therefore in the overall polymer molecular weight distribution, of the formulation over time at all three of the different temperatures; the peak indicated a broad MW distribution, from more than 870 kDa to about 40 kDa, with a maximum at about 520 kDa. The MW distribution was evaluated by comparison with standard references with well-determined MW. The small shoulder detected in the left part of the peak was ascribable to collagen. The data suggested that the formulation is stable under normal storage conditions for up to 12 weeks (data not shown).

Figure 16:
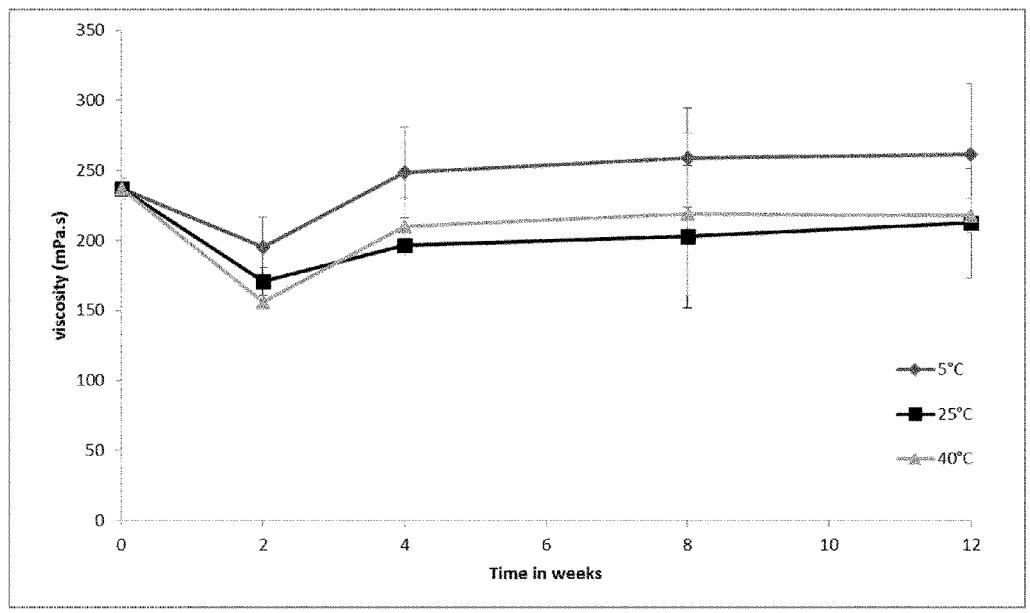
FIG. 16 a: intrinsic viscosity variation, calculated as mean±standard deviation within the shear rate of 10-50 s$^{-1}$, of the freeze-dried (FD) formulation over time in 3-month stability in normal storage conditions (5° C.), accelerated conditions (25° C.) and stressed conditions (40° C.).
Figure 16:
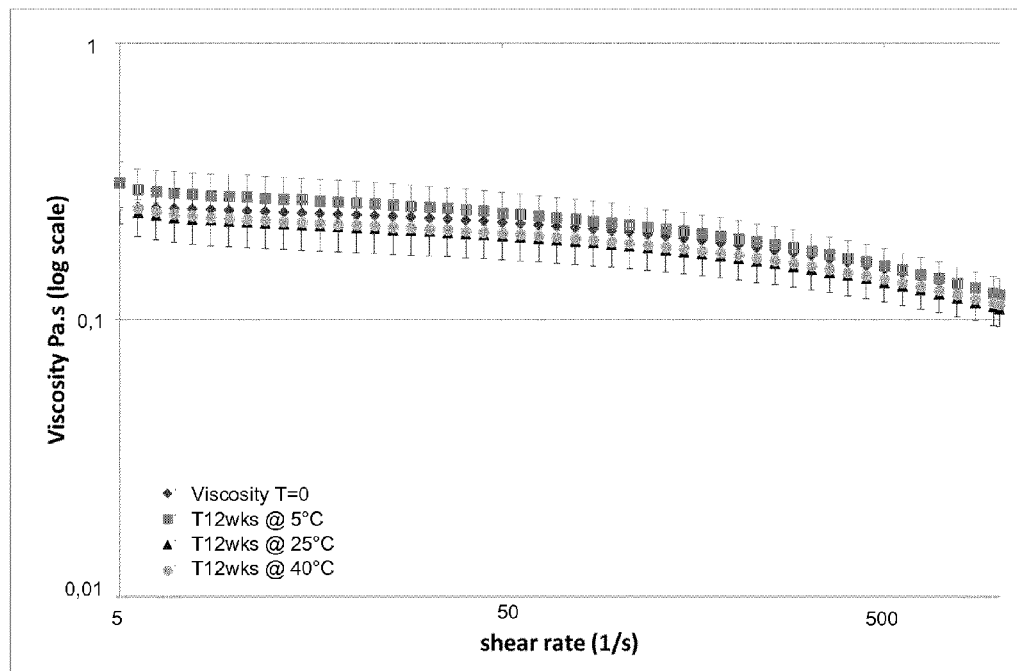

Viscosity:

A slight decrease in the viscosity of the formulation were observed with respect to time zero for samples stored at 25° C. and 40° C., due to accelerating degradation conditions, while no significant differences were observed for samples stored at normal conditions (2-8° C.); the variations observed were most likely related to the variability of the method and the filling process. The data suggested that the formulation is stable under normal storage conditions for up to 12 weeks (see FIG. 16).

Figure 17:
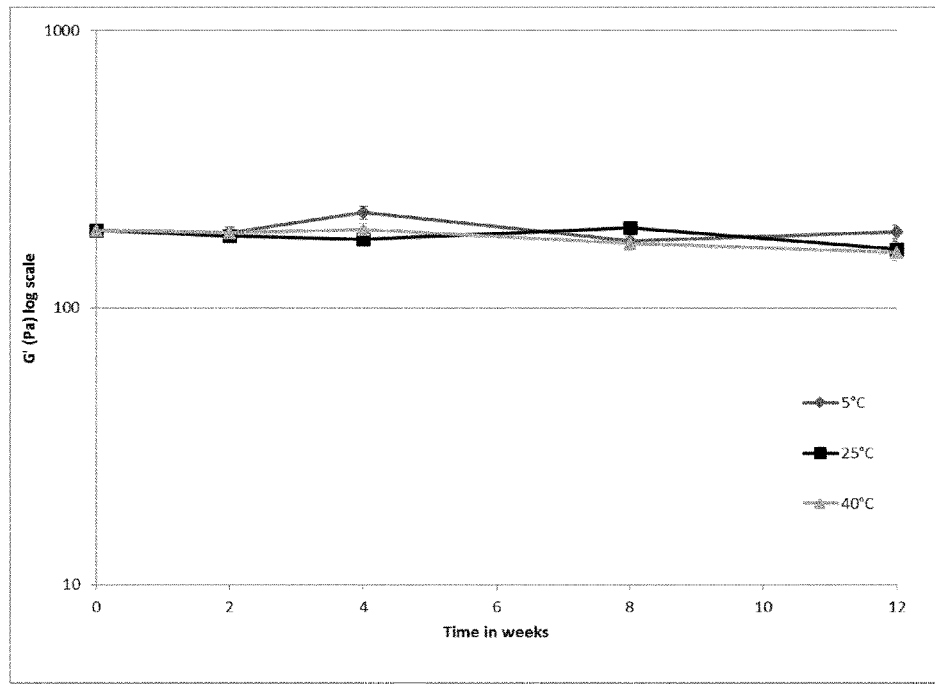
FIGS. 17 a and 17 b: mechanical properties evaluation.
Figure 17:
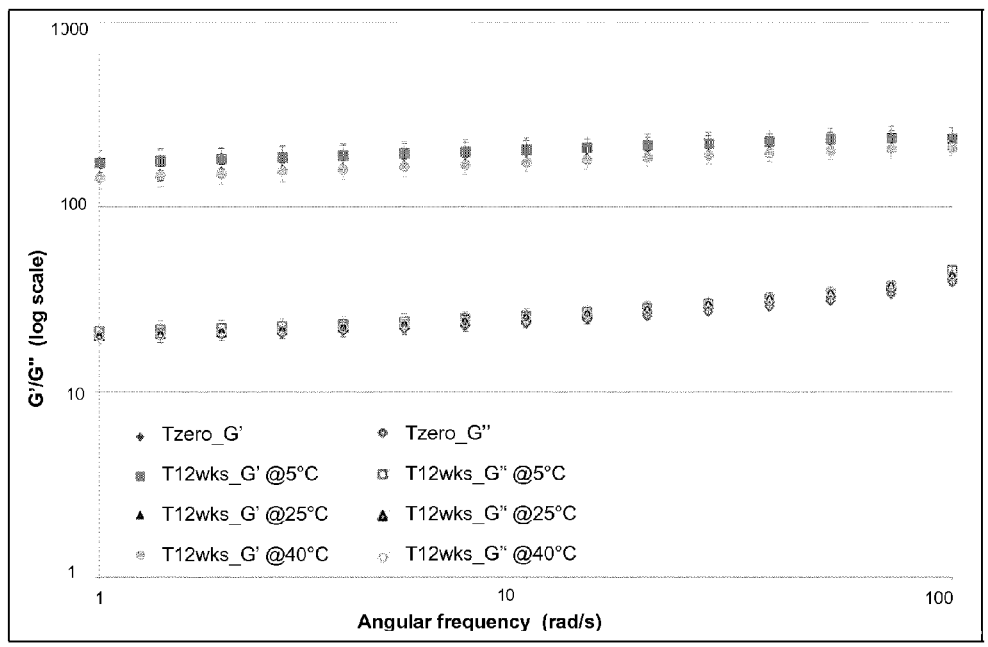

Mechanical Properties:

Alginate FD formulation, reconstituted with water at each time point of the stability study, was used to form the hydrogel, by mixing with calcium chloride solution. The mechanical properties of the obtained hydrogel were investigated. No changes were observed in the storage modulus G', and therefore in the mechanical properties, over time at all three of the different temperatures. The results presented in FIG. 17 suggested that the formulation is stable under the normal storage conditions for up to 12 weeks.

Cell Invasion Capability:

Alginate FD formulation, reconstituted with water at each time point of the stability study, was used to form the hydrogel, by mixing with calcium chloride solution. The cell invasion capability of the obtained hydrogel was investigated, incubating the hydrogels with the cells during 72 hours and then analyzing the samples by Confocal Laser Scanning Microscopy. No significant variations were observed in the number of living cells able to penetrate in the hydrogel matrix over time, considering samples stored in the same temperature conditions (data not shown). At each time point, samples stored at 40° C. showed higher numbers of penetrating cells than samples stored at 2-8° C., suggesting that incubation at a high temperature caused partial alteration of the polymer matrix. The data suggested that the formulation is stable under normal storage conditions for up to 12 weeks.

CONCLUSION

Freeze-dried alginate formulation showed good stability in normal storage conditions (2-8° C.) for up to 12 weeks, and appeared to be at least as stable as the corresponding liquid formulation.

Tables

TABLE 1

Composition of calcium and polymer liquid solutions of four candidate alginate-based formulations

| Candidate formulations | CaCl2 (S2) (mg/mL) | Polymer liquid solution (alginate) in milliQ water (S1) | | | | | | S1:S2 (v:v) | Final gel | |
|---|---|---|---|---|---|---|---|---|---|---|
| | | Alginate (% wt) | Sucrose (mg/mL) | Collagen (µg/mL) | FGF-18 (µg/mL) | pH | Osm (mOsm/kg) | | FGF-18 (µg/mL) | pH |
| 1 | 10 | 4 | 70 | 1 | 54 | 6.9 | 315 | 2:1 | 36 | 7 |
| 2 | 10 | 4 | 70 | 2 | 54 | 7.3 | 318 | 2:1 | 36 | 7 |
| 3 | 10 | 3 | 70 | 1 | 54 | 6.9 | 296 | 2:1 | 36 | 7 |
| 4 | 10 | 3 | 70 | 2 | 54 | 6.9 | 304 | 2:1 | 36 | 7 |

TABLE 2

Gelation time of active alginate-based formulations

| | Gelation time at 37° C. | |
|---|---|---|
| Candidate formulations | Gel prepared in Petri dish (subsequent additions) | Gel prepared with syringe connector device (mixing) |
| 1 | 5 min | instantaneous |
| 2 | <5 min | instantaneous |
| 3 | 15 min | instantaneous |
| 4 | 15 min | instantaneous |

TABLE 3

Gelation time at 37° C. of selected chitosan-based formulations

| Formulation | Chitosan MW and DD | Chitosan (% wt) | B-GP (% wt) | HEC (% wt) | KH2PO4 (mM) | pH | Osmolality (mOsm/kg) | Gelation time |
|---|---|---|---|---|---|---|---|---|
| I | HMW 75% | 1.8 | 50 | / | / | / | / | 5 min |
| II | HMW 75% | 2 | 6.9 | / | / | 7.2 | / | 2 h |
| III | HMW 75% | 2 | 1.2 | 0.5 | / | 6.1 | / | 25 min |
| IV | HMW 75% | 1.5 | 1.7 | 0.5 | / | 6.1 | / | 13 min |
| V | HMW 75% | 1.5 | 1.6 | 0.25 | / | 6.2 | / | 19 min |
| VI | HMW 75% | 1.6 | 1.6 | 0.25 | / | 6.3 | / | 30 min |
| VII | HMW 75% | 1.8 | 1.5 | 0.5 | / | 6.3 | / | 12 min |
| VIII | HMW 75% | 1.8 | 1.7 | 0.1 | / | 6.4 | / | 50 min |
| IX | HMW 95% | 1.0 | 2.5 | / | 0 | 6.8 | 384 | 24 h |
| X | LMW 75% | 2.0 | 2.1 | / | 10 | 7.0 | 346 | 3 h |
| XI | LMW 75% | 2.0 | 2.5 | / | 10 | 6.9 | 379 | 2 h |

REFERENCES

1. Ellsworth et al., 2002, Osteoarthritis and Cartilage 10:308-320
2. Shimoaka et al., 2002, JBC 277(9):7493-7500
3. WO2008/023063
4. WO2004/032849
5. WO2012/172072
6. J. Ringe et al., 2012, Nature Reviews Rheumatology 8(8):493-498
7. C. Dispenza et al., 2011, Polym. Chem., 2:192-202
8. J. K. Tessmar, A. M. Göpferich, 2007, Adv. Drug Delivery Rev. 59:274-291
9. C. Lo Presti et al., 2011, Reactive & Functional Polymers 71:155-167
10. WO2008/063418
11. S. R. Van Tomme et al., 2008, Int. J. Pharm. 355:1-18
12. WO98/16644
13. WO2006/063362
14. Custers et al., 2007, Osteoarthritis and Cartilage 15:1241-1248
15. Rayatpisheh et al., 2011, J. Biomed. Mater. Res. 98A:235-244
16. Tsai et al., 1998, Biotech. Techniques 12:21-23
17. Cheng et al., 2010, Tissue Engineering 16A:695-703
18. Schuetz et al., 2008, Eur. J. Pharm. Biopharm. 68:19-25
19. Yan et al., 2010, J. Biomat. Appl. 24:625-637
20. Ahmadi et al., 2008, J. Biomed. Mater. Res. 86A:824-832
21. Hoemann et al., 2007, J. Biomed. Mater Res. 83A:521-529
22. Filion et al. 2007, Biomacromol. 8:3224-3234
23. Anseth et al., 1996, Biomaterials 17:1647-1657
24. Peppas et al., 2000, Eur. J. Pharm. Biopharm. 50:27-46
25. Dang et al., 2011, Carbohydrate Polymers 83:171-178
26. WO2012/113812

The invention claimed is:

1. A homogenous hydrogel comprising FGF-18, alginate, collagen, sucrose, and a dicationic salt, wherein FGF-18 is selected from the group consisting of:

a) a polypeptide comprising the amino acid residues 28-207 of SEQ ID NO: 1, b) a polypeptide comprising the amino acid residues 28-196 of SEQ ID NO: 1, and c) a polypeptide comprising SEQ ID NO: 2.

2. The homogeneous hydrogel according to claim 1, wherein said hydrogel is formed from two solutions:

a) a first homogeneous solution (solution 1) comprising FGF-18, alginate, collagen and sucrose, and
   b) a second solution (solution 2) comprising a dicationic salt.

3. The homogeneous hydrogel according to claim 2, wherein solution 1 and solution 2 are combined in a ratio of solution 1:solution 2 of 2:1 (volume to volume).

4. The homogeneous hydrogel according to claim 2, wherein alginate is at a concentration of 3 to 4% wt, collagen is at a concentration of 1 to 2 mcg/mL, sucrose is at a concentration of 10 to 100 mg/mL, and salt is at a concentration of 1 to 20 mg/mL in their respective solutions.

5. The homogeneous hydrogel according to claim 1, wherein the dicationic salt is a calcium salt, magnesium salt, copper salt or zinc salt.

6. The homogeneous hydrogel according to claim 1, wherein alginate is at a concentration of 3 to 4% wt, collagen is at a concentration of 1 to 2 mcg/mL, sucrose is at a concentration of 10 to 100 mg/mL, and salt is at a concentration of 1 to 20 mg/mL.

7. A method for producing a homogeneous hydrogel, comprising the steps of:
   a) preparing a first homogeneous solution (solution 1) comprising FGF-18, alginate, collagen and sucrose,
   b) preparing a second solution (solution 2) comprising a dicationic salt,
   c) mixing the 2 solutions before injection or co-injecting both solutions to form the hydrogel,
wherein FGF-18 is selected from the group consisting of:
a) a polypeptide comprising the amino acid residues 28-207 of SEQ ID NO:1,
b) a polypeptide comprising the amino acid residues 28-196 of SEQ ID NO: 1, and
c) a polypeptide comprising SEQ ID NO: 2.

8. The method according to claim 7, wherein the dicationic salt is a calcium salt, magnesium salt, copper salt or zinc salt.

9. The method according to claim 7, wherein the solutions are mixed in a ratio of solution 1:solution 2 of 2:1 (volume to volume).

10. The method according to claim 7, wherein the solutions are co-injected in a ratio of solution 1:solution 2 of 2:1 (volume to volume).

11. An article of manufacture comprising two containers, wherein:
   a) the first container comprises a first homogeneous solution (solution 1), wherein said first solution comprises FGF-18, alginate, collagen and sucrose, and
   b) the second container comprises a second solution (solution 2), said second solution comprising a dicationic salt,
wherein FGF-18 is selected from the group consisting of:
a) a polypeptide comprising the amino acid residues 28-207 of SEQ ID NO: 1,
b) a polypeptide comprising the amino acid residues 28-196 of SEQ ID NO: 1, and
c) a polypeptide comprising SEQ ID NO: 2.

12. The article of manufacture according to claim 11, wherein the dicationic salt is a calcium salt, magnesium salt, copper salt or zinc salt.

13. The article of manufacture according to claim 11, wherein alginate is at a concentration of 3 to 4% wt, collagen is at a concentration of 1 to 2 mcg/mL, sucrose is at a concentration of 10 to 100 mg/mL, and salt is at a concentration of 1 to 20 mg/mL.

14. The article of manufacture according to claim 11, wherein the ratio solution 1:solution 2 is 2:1 (volume to volume).

15. The article of manufacture according to claim 11, wherein the first container and the second container are the two compartments of a dual-chamber system or of a dual-needle injection device.

* * * * *

UNITED STATES PATENT AND TRADEMARK OFFICE
CERTIFICATE OF CORRECTION

PATENT NO. : 9,795,714 B2  
APPLICATION NO. : 15/105710  
DATED : October 24, 2017  
INVENTOR(S) : Fabiana Canal and Caterina Lo Presti Page 1 of 1

It is certified that error appears in the above-identified patent and that said Letters Patent is hereby corrected as shown below:

In the Specification

Column 18,
Line 22, "13-GP" should read --β-GP--.

Signed and Sealed this
Twenty-sixth Day of June, 2018

Andrei Iancu
*Director of the United States Patent and Trademark Office*

```
                        SEQUENCE LISTING

<160> NUMBER OF SEQ ID NOS: 2

<210> SEQ ID NO 1
<211> LENGTH: 207
<212> TYPE: PRT
<213> ORGANISM: Homo sapiens
<220> FEATURE:
<223> OTHER INFORMATION: human FGF-18

<400> SEQUENCE: 1

Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
                20                  25                  30

Phe Arg Ile His Val Glu Asn Gln Thr Arg Ala Arg Asp Asp Val Ser
            35                  40                  45

Arg Lys Gln Leu Arg Leu Tyr Gln Leu Tyr Ser Arg Thr Ser Gly Lys
        50                  55                  60
```

```
His Ile Gln Val Leu Gly Arg Arg Ile Ser Ala Arg Gly Glu Asp Gly
 65                  70                  75                  80

Asp Lys Tyr Ala Gln Leu Leu Val Glu Thr Asp Thr Phe Gly Ser Gln
                 85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
            115                 120                 125

Phe Ile Glu Lys Val Leu Glu Asn Asn Tyr Thr Ala Leu Met Ser Ala
130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
                180                 185                 190

Thr Val Thr Lys Arg Ser Arg Arg Ile Arg Pro Thr His Pro Ala
                195                 200                 205

<210> SEQ ID NO 2
<211> LENGTH: 170
<212> TYPE: PRT
<213> ORGANISM: Artificial
<220> FEATURE:
<223> OTHER INFORMATION: recombinant truncated FGF-18(sprifermin)

<400> SEQUENCE: 2

Met Glu Glu Asn Val Asp Phe Arg Ile His Val Glu Asn Gln Thr Arg
1               5                   10                  15

Ala Arg Asp Asp Val Ser Arg Lys Gln Leu Arg Leu Tyr Gln Leu Tyr
                20                  25                  30

Ser Arg Thr Ser Gly Lys His Ile Gln Val Leu Gly Arg Arg Ile Ser
            35                  40                  45

Ala Arg Gly Glu Asp Gly Asp Lys Tyr Ala Gln Leu Leu Val Glu Thr
50                  55                  60

Asp Thr Phe Gly Ser Gln Val Arg Ile Lys Gly Lys Glu Thr Glu Phe
65                  70                  75                  80

Tyr Leu Cys Met Asn Arg Lys Gly Lys Leu Val Gly Lys Pro Asp Gly
                85                  90                  95

Thr Ser Lys Glu Cys Val Phe Ile Glu Lys Val Leu Glu Asn Asn Tyr
            100                 105                 110

Thr Ala Leu Met Ser Ala Lys Tyr Ser Gly Trp Tyr Val Gly Phe Thr
            115                 120                 125

Lys Lys Gly Arg Pro Arg Lys Gly Pro Lys Thr Arg Glu Asn Gln Gln
            130                 135                 140

Asp Val His Phe Met Lys Arg Tyr Pro Lys Gly Gln Pro Glu Leu Gln
145                 150                 155                 160

Lys Pro Phe Lys Tyr Thr Thr Val Thr Lys
                165                 170
```